(12) United States Patent
Mevorach

(10) Patent No.: US 9,567,568 B2
(45) Date of Patent: Feb. 14, 2017

(54) METHOD OF PREPARING APOPTOTIC MONOCYTES

(71) Applicant: Enlivex Therapeutics Ltd., Jerusalem (IL)

(72) Inventor: Dror Mevorach, Jerusalem (IL)

(73) Assignee: ENLIVEX THERAPEUTICS LTD., Jerusalem (IL)

( * ) Notice: Subject to any disclaimer, the term of this patent is extended or adjusted under 35 U.S.C. 154(b) by 0 days.

(21) Appl. No.: 14/499,279

(22) Filed: Sep. 29, 2014

(65) Prior Publication Data

US 2015/0056678 A1 Feb. 26, 2015

Related U.S. Application Data

(62) Division of application No. 11/121,048, filed on May 4, 2005, now abandoned.

(51) Int. Cl.
| | |
|---|---|
| *C12N 5/0786* | (2010.01) |
| *A61K 35/15* | (2015.01) |
| *A61K 35/26* | (2015.01) |
| *A61K 39/00* | (2006.01) |
| *A61M 1/34* | (2006.01) |
| *A61K 41/00* | (2006.01) |
| *C12N 13/00* | (2006.01) |
| *A61M 1/36* | (2006.01) |

(52) U.S. Cl.
CPC ............ *C12N 5/0645* (2013.01); *A61K 35/15* (2013.01); *A61K 35/26* (2013.01); *A61K 39/0008* (2013.01); *A61K 41/0023* (2013.01); *A61M 1/3472* (2013.01); *A61M 1/3486* (2014.02); *C12N 13/00* (2013.01); *A61K 2039/515* (2013.01); *A61M 1/3681* (2013.01); *C12N 2500/90* (2013.01)

(58) Field of Classification Search
None
See application file for complete search history.

(56) References Cited

U.S. PATENT DOCUMENTS

| | | |
|---|---|---|
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,666,828 A | 5/1987 | Gusella |
| 4,683,202 A | 7/1987 | Mullis |
| 4,801,531 A | 1/1989 | Frossard |
| 4,838,852 A | 6/1989 | Edelson et al. |
| 4,879,219 A | 11/1989 | Wands et al. |
| 5,011,771 A | 4/1991 | Bellet et al. |
| 5,192,659 A | 3/1993 | Simons |
| 5,272,057 A | 12/1993 | Smulson et al. |
| 5,281,521 A | 1/1994 | Trojanowski et al. |
| 5,591,457 A | 1/1997 | Bolton |
| 5,951,509 A | 9/1999 | Morris |
| 5,985,914 A | 11/1999 | Zeldis et al. |
| 6,219,584 B1 | 4/2001 | Lee |
| 6,354,297 B1 | 3/2002 | Eiseman |
| 6,607,722 B2 | 8/2003 | Edelson et al. |
| 7,109,031 B2 | 9/2006 | Edelson et al. |
| 7,989,203 B2 * | 8/2011 | Albert ............... A61K 39/0008 435/347 |
| 2005/0031618 A1 | 2/2005 | Mevorach |
| 2005/0202098 A1 | 9/2005 | Mevorach |

FOREIGN PATENT DOCUMENTS

| | | |
|---|---|---|
| WO | WO 97/38707 | 10/1997 |
| WO | WO 99/35493 | 7/1999 |
| WO | WO 02/060376 | 8/2002 |
| WO | WO 2006/117786 | 11/2006 |

OTHER PUBLICATIONS

Hashimoto, S., et al. J. Immunol. 2001;167:3619-3625.*
Heidenreich, S., et al. J. Immunol. 1997;159:3178-3188.*
Bohnenkamp, H.R., et al. J. Immunol. Methods 2004;294:67-80.*
Abboud CN, et al. (2000) In: Hoffman ea, ed. Hemotology, Basic Principles and Practice London: Churchill Livingstone, 22-244.
Accorsi et al. (2001) "Large Volume Leukapheresis With AMICUS Cell Separator in Peripheral Blood Stem Cell Autologous Transplant", Transfusion and Apheresis Science, 24:79-83.
Albert ML, et al. (1998) Dendritic cells acquire antigen from apoptotic cells and induce class I-restricted CTLs. Nature; 392 (6671):86-9.
Andrade et al., (2000) Apoptosis in systemic lupus erythematosus. Clinical implications. Rheum Dis Clin North Am 26 (2): 215-27.
Andrei et al. (1999) "The Secretory Route of the Leaderless Protein Interleukin 1 p Involves Exocytosis of Endolysosome-Related Vesicles", Molecular Biology of the Cell, 10:1463-1475.
Baran J, et al. (2001) "Fas (CD95)—Fas ligand interactions are responsible for monocyte apoptosis occurring as a result of phagocytosis and killing of *Staphylococcus aureus*". Infect Immun; 69 (3):1287-97.
Bergmann MW, et al. (2001) "The proteosome inhibitor, P.S.-341 inhibits growth, induces apoptosis and overcomes drug resistance in humah multiple myeloma cells". Cancer Research; 61:3071-6.
Beyth et al. (2005) "Human Mesenchymal Stem Cells Alter Antigen—Presenting Cell Maturation and Induce T-Cell Unresponsiveness", Blood, 105: 2214-2219.

(Continued)

*Primary Examiner* — Gerald R Ewoldt
(74) *Attorney, Agent, or Firm* — Mark S. Cohen; Pearl Cohen; Zedek Latzer Baratz LLP

(57) ABSTRACT

A method of isolating monocyte populations of cells and inducing apoptosis in these populations without production of pro-inflammatory mediators is disclosed. The method comprises isolating the monocytes and, subjecting them to substrate-adherence and serum deprivation conditions. Apoptotic monocytes as prepared are useful for treating inflammation-associated diseases.

2 Claims, 12 Drawing Sheets

(56) References Cited

OTHER PUBLICATIONS

Burgstaler et al. (2004) "Hematopoietic Progenitor Cell Large Volume Leukapheresis (LVL) on the Fenwal Amicus Blood Separator", Journal of Clinical Apheresis, 19:103-111.
Caricchio et al., (2003) "Ultraviolet B Radiation-Induced Cell Death: Critical Role of Ultraviolet Dose in Inflammation and Lupus Autoantigen Redistribution". The Journal of Immunology 171: 5778-5786.
Chang et al. (2001) "Mammalian MAP Kinase Signalling Cascades", Nature, 410:37-40.
Chen et al., (2001) "TGF-beta released by apoptotic T cells contributes to an immunosuppressive milieu." Immunity 14 (6): 715-25.
Cobb MH. (1999) "MAP kinase pathways." Prog Biophys Mol Biol; 71 (3-4):479-500.
De Carvalho Bittencourt et al. (2001) "Intravenous Injection of Apoptotic Leukocytes Enhances Bone Marrow Engraftment Across Major Histocompatibility Barriers", Blood, 98: 224-230. Abstract and Introduction.
Dinarello CA. (1996) "Biologic basis for interleukin-1 in disease." Blood; 87 (6):2095-147.
Dinarello CA. (1998) "Interleukin-1, interleukin-1 receptors and interleukin-1 receptor antagonist." Int Rev Immunol; 16 (5-6):457-99.
Elhalel et al.(2003) "CTLA-4. FasL Induces Alloantigen-Specific Hyporesponsiveness", The Journal of Immunology, 170: 5842-5850.
Fadok et al. (1992) "Exposure of Phosphatidylserine on the Surface of Apoptotic Lymphocytes Triggers Specific Recognition and Removal by Macrophages", The Journal of Immunology, 148(7):2207-2216.
Fadok et al. (1998)"Macrophages That Have Ingested Apoptotic Cells in Vitro Inhibit Proinflammatory Cytokine Production Through Autocrine/Paracrine Mechanisms Involving TGF-p, PGE2, and PAF", Journal of Clinical Investigation, 101(4):890-898.
Fahy RJ, et al. (1999) "Spontaneous human monocyte apoptosis utilizes a caspase-3-dependent pathway that is blocked by endotoxin and is independent of caspase-1." J Immunol; 163 (4):1755-62.
Gribben et al., (1996) Complete blockade of B7 family-mediated costimulation is necessary to induce human alloantigen-specific anergy: a method to ameliorate graft-versus-host disease and extend the donor pool. Blood 87(11): 4887-93.
Guinan et al., (1999) "Transplantation of anergic histoincompatible bone marrow cells." N Engl J Med 341:1081-1082.
Hamada et al., (1998) "Involvement of Mac-1-mediated adherence and sphingosine 1-phosphate in survival of phorbol ester-treated U937 cells." Biochem Biophys Res Commun 244: 745-50.
Henson et al. (2001) "Apoptotic Cell Removal", Current Biology, 11:795-805.
Herrmann et al., (1998) "Impaired phagocytosis of apoptotic cell material by monocyte-derived macrophages from patients with systemic lupus erythematosus." Arthritis Rheum 41(7): 1241-50.
Huynh ML, et al. (2002) "Phosphatidylserine-dependent ingestion of apoptotic cells promotes TGF-beta1 secretion and the resolution of inflammation." J Clin Invest; 109 (1):41-50.
Iwai et al. (1994) "Differential Expression of bc1-2 and Susceptibility to Anti-Fas—Mediated Cell Death in Peripheral Blood Lymphocytes, Monocytes, and Neutrophils", Blood, 84(4): 1201-1208.
Kiener et al. (1997) "Differential Induction of Apoptosis by Fas-Fas Ligand Interactions in Human Monocytes and Macrophages", J. Exp. Med. , 185(8):1511-1516.
Kleinclauss et al., (2003) "Administration of donor apoptotic cells: an alternative cell-based therapy to induce tolerance?" Transplantation 75(9 Suppl): 43S-45S.
Koh et al. (2000) "Cytokine Dysregulation Induced by Apoptotic Cells is a Shared Characteristic of Murine Lupus", The Journal of Immunology, 165: 4190-4201.
Laderach et al. (1998) "Nucleosomes Inhibit Phagocytosis of Apoptotic Thymocytes by Peritoneal Macrophages From MRL+/+ Lupus-Prone Mice", Journal of Leukocyte Biology, 64: 774-780.

Lauber et al., (2003) "Apoptotic cells induce migration of phagocytes via caspase-3-mediated release of a lipid attraction signal." Cell 113 (6): 717-30.
Licht et al. (2004) "Decreased Phagocytosis of Apoptosis of Apoptotic Cells in Diseased SLE Mice", Journal of Autoimmunity, 22: 139-145.
Liu et al. (2002) "Immune Tolerance After Delivery of Dying Cells to Dendritic Cells In Situ", J Exp Med, 196: 1091-1097.
Mackenzie A, et al. (2001) "Rapid secretion of interleukin-1beta by microvesicle shedding." Immunity; 15 (5):825-35.
Mangan et al. (1991) "Differential Regulation of Human Monocyte Programmed Cell Death (Apoptosis) by Chemotactic Factors and Pro-Inflammatory Cytokines", The Journal of Immunology, 147(10):3408-3412.
Mangan et al. (1991) "Lipopolysaccharide, Tumor Necrosis Factor a, and IL-1(3 Prevent Programmed Cell Death (Apoptosis) in Human Peripheral Blood Monocytes", The Journal of Immunology, 146(5): 1541-1546.
Mansouri A, et al. (2003) "Sustained activation of JNK/p38 MAPK pathways in response to cisplatin leads to Fas ligand induction and cell death in ovarian carcinoma cells." J Biol Chem; 278 (21):19245-56.
Marsden and Strasser (2003) "Control of apoptosis in the immune system: Bcl-2, BH3—only proteins and more." Annu Rev Immunol 21:71-105.
Matthew et al. (1998) "Dendritic Cells Acquire Antigen From Apoptotic Cells and Induce Class IRestricted CTLs", Nature, 392:86-89.
Mevorach (1999) "The Immune Response to Apoptotic Cells", Annals of the N.Y. Academy of Sciences, 887: 191-198. Abstract.
Mevorach (2000) "Opsonization of Apoptotic Cells. Implications for Uptake and Autoimmunity", Annals of the N.Y. Academy of Sciences, 926: 226-235. Abstract.
Zanke BW,et al. (1996) "The stress-activated protein kinase pathway mediates cell death following injury induced by cis-platinum, UV irradiation or heat." Curr Biol; 6 (5):606-13.
Mevorach et al. (1998) "Systemic Exposure to Irradiated Apoptotic Cells Induces Autoantibody Production", J Exp Med, 188(2): 387-392.
Mevorach et al., (1998) "Complement-dependent clearance of apoptotic cells by human macrophages." J Exp Med 188 (12): 2313-20.
Miwa K, et al. (1998) "Caspase 1-independent IL-1beta release and inflammation induced by the apoptosis inducer Fas ligand." Nat Med; 4 (11):1287-92.
Molinari E, et al. (1999) "Proteasome-mediated degradation of transcriptional activators correlates with activation domain potency in-vivo." Embo J; 18 (22):6439-47.
Park DR, et al. (2003) "Fas (CD95) induces proinflammatory cytokine responses by human monocytes and monocyte-derived macrophages." J Immunol; 170 (12):6209-16.
Paz-Miguel et al. (1999) "Reactive Oxygen Intermediates During Programmed Cell Death Induced in the Thymus of the Ts(17/16)65Dn Mouse, A Murine Model for Human Down's Syndrome", The Journal of Immunology, 163: 5399-5410.
Perlman H,et al. (1999) "FLICE-inhibitory protein expression during macrophage differentiation confers resistance to fas-mediated apoptosis." J Exp Med; 190 (11):1679-88.
Perruche et al. (2004) "Intravenous Infusion of Apoptotic Cells Simultaneously With Allogeneic Hematopoietic Grafts Alters Anti-Donor Humoral Immune Responses", American Journal of Transplantation, 4: 1361-1365.
Ponner et al. (1998) "Induction of Apoptosis Reduces Immunogenicity of Human T-Cell Lines in Mice", Scandavian Journal of Immunology, 47(4): 343-347.
Potapova O, et al. (1997) "The Jun kinase/stress-activated protein kinase pathway functions to regulate DNA repair and inhibition of the pathway sensitizes tumor cells to cisplatin." J Biol Chem; 272 (22):14041-4.
Restifo NP. (2000) "Not so Fas: Re-evaluating the mechanisms of immune privilege and tumor escape." Nat Med; 6 (5):493-5.

(56) References Cited

OTHER PUBLICATIONS

Rubartelli A, et al. (1997) "Secretion of mammalian proteins that lack a signal sequence. Unusual Secretory Pathways: From Bacteria to Man" Austin, TX: R. G. Landes Co.

Sanchez-Perez I, et al. (1998) "Cisplatin induces a persistent activation of JNK that is related to cell death." Oncogene; 16 (4):533-40.

Sauter et al., (2000) "Consequences of cell death: exposure to necrotic tumor cells, but not primary tissue cells or apoptotic cells, induces the maturation of immunostimulatory dendritic cells." J Exp Med 191 (3): 423-34.

Savill (2001) "Phagocyte clearance of cells dying by apoptosis and the regulation of glomerular inflammation." Adv Nephrol Necker Hosp 31: 21-8.

Savill et al., (2002) "A blast from the past: clearance of apoptotic cells regulates immune responses." Nat Rev Immunol 2 (12):965-75.

Schwartz (2003) "T cell anergy." Annu Rev Immunol 21: 305-34.

Shoshan Y, et al. (2001) "Accelerated Fas-mediated apoptosis of monocytes and maturing macrophages from patients with systemic lupus erythematosus: relevance to in-vitro impairment of interaction with iC3b-opsonized apoptotic cells." J Immunol; 167 (10):5963-9.

Tan et al. (1993) "Induction of Alloantigen-Specific Hyper-responsiveness in Human T Lymphocytes by Blocking Interaction of CD28 With Its Natural Ligand B7/BB1", J Exp Med, 177: 165-173.

Tan et al., (2005) "Creation of tolerogenic human dendritic cells via intracellular CTLA4: a novel strategy with potential in clinical immunosuppression." Blood 106(9): 2936-43.

Trebeden-Negre et al. (2003) "B Cells Apoptosis Accelerates the Onset of Murine Lupus", European Journal of Immunology, 33: 1603-1612.

UDA (1993) "The Specific MLR Inhibiting Factors Induced by the Portal Venous Inoculation of Ultraviolet-B Irradiated Spleen Cells in Primates", Transplant, 28(6): 677-684.

Um HD, et al. (1996) "Fas mediates apoptosis in human monocytes by a reactive oxygen intermediate dependent pathway." J Immunol; 156 (9):3469-77.

Vandivier RW, et al. (2002) "Elastase-mediated phosphatidylserine receptor cleavage impairs apoptotic cell clearance in cystic fibrosis and bronchiectasis." J Clin Invest; 109 (5):661-70.

Verbovetski et al., (2002) "Opsonization of apoptotic cells by autologous iC3b facilitates clearance by immature dendritic cells, down-regulates DR and CD86, and up-regulates CC chemokine receptor 7." J Exp Med 196 (12): 1553-61.

Voll et al., (1997) "Immunosuppressive effects of apoptotic cells." Nature 390 (6658): 350-1.

Waller et al. (1999) "Irradiated Donor Leukocyte's Promote Engraftment of Allogeneic Bone Marrow in Major Histocompatibility Complex Mismatched Recipients Without Causing Graft-Versus-Host Disease", Blood, 94(9): 3222-3233.

Yaron et al. (1969) "Leukocyte-Connective Tissue Cell Interaction. I. Stimulation of Hyaluronate Synthesis by Live and Dead Leukocytes", Arthritis and Rheumatism, 12: 365-373.

McLeod; "Rationales for therapeutic apheresis", Hematology. 2005; 10 Suppl 1:203-7.

* cited by examiner

METHOD OF PREPARING APOPTOTIC MONOCYTES

CROSS-REFERENCE TO RELATED APPLICATIONS

This application is a divisional of U.S. patent application Ser. No. 11/121,048 filed May 4, 2005, and published as US 2005/0202098 on Sep. 15, 2009, which is hereby incorporated by reference.

FIELD AND BACKGROUND OF THE INVENTION

The present invention relates to methods of using dying cells for treating diseases characterized by pathological immune responses, and to devices for preparing such dying cells. More particularly, the present invention relates to methods of using apoptotic leukocytes for treating diseases characterized by pathological immune responses, such as autoimmune diseases and transplantation-related diseases, and to devices for preparing such apoptotic leukocytes.

Diseases characterized by pathological immune responses include a large number of diseases which are associated with significant mortality and morbidity, and for which no satisfactory/optimal treatments are available. Such diseases particularly include autoimmune diseases, such as systemic lupus erythematosus (SLE), transplantation-related diseases such as graft-versus-host disease (GVHD).

The immune system is a complex network comprising cells, antibodies, tissues, and chemical messenger molecules which allow for communication between these structures. A hallmark of a healthy immune system is the ability to recognize bacteria, viruses, and other foreign bodies and to effectively attack such pathogens while continuing to distinguish between the foreign bodies and the molecules, cells, tissues and organs of the body. In addition to fighting infections, the immune system has other roles in maintaining the normal state of health and function of the body. Throughout the life span of an organism, tissues become reshaped with areas of cells being removed. This is accomplished by a process termed programmed cell death or apoptosis, the apoptotic cells disintegrating in an orderly and harmless fashion and being phagocytosed. In many organs, for example, a certain percentage of the cells die off every day while different branches of the immune system are typically called in to remove the dead cells and parts thereof to make room for the new cells which arise to replace them. Were it not for the cellular debris-removing cells of the immune system, typically macrophages, tissue and organ growth would be impossible due to a lack for space. The process of apoptosis is furthermore considered to be particularly important in the development and maintenance of the immune system itself, where the immune cells which recognize or attack normal cells of the body are destroyed and removed by this process.

The number of monocytes, neutrophils, and lymphocytes that are produced, circulating, dying, and extravasating in the body is controlled at various levels, including via apoptosis.

In the case of monocytes, CFU-GM, the earliest identified cell committed to differentiate along the myeloid pathway, develops into monocyte in the bone marrow, mainly in the presence of M-CSF, IL-3, and low levels of GM-CSF. No bone marrow reserve exists for monocytes, which spend 1-3 days in transit through the marrow and are then released to spend from 8 to 72 hours in the blood, with subsequent further possible differentiation, maturation, and proliferation in tissues [1]. Monocytes comprise 1-6 percent of peripheral leukocytes, and it is estimated that $5.7\times10^6$ monocytes/kg are produced every day. Monocytes can survive in tissues as macrophages for long periods, but a substantial portion of monocytes are constantly undergoing apoptosis, either in the absence of anti-apoptotic factors or following infection or activation.

Monocytes express Fas and Fas ligand irrespective of their state of activation [2, 3], and were shown to undergo Fas-dependent apoptosis upon culture [3], activation [4], or infection [5]. Monocytes can be rescued from apoptosis upon exposure to growth factors, differentiating factors (GM-CSF and IL-4), or activation factors [3, 6-8]. Upon differentiation to macrophages, monocytes are rescued from Fas-dependent apoptosis by the expression of Fas-associated death domain-like IL-1-beta-converting enzyme-inhibitory protein (FLIP) [3, 9].

Neutrophils constitute the most abundant population of leukocytes. In humans, the daily turnover of neutrophils is about $1.6\times10^9$ cells/kg body weight (Klebanoff S J, Clark R X: The Neutrophil: Function and Clinical Disorders. Amsterdam, North-Holland Publishing, 1978, p 313), which keeps the number of mature neutrophils within defined limits despite the tremendous proliferative potential of the bone marrow precursor cells. This large turnover is mediated by the continuous egress of neutrophils from the circulation. Neutrophils do not return to the circulation but are eliminated by secretion in mucosa or die in the tissues within 1-2 days (Klebanoff S J, Clark R X: The Neutrophil: Function and Clinical Disorders. Amsterdam, North-Holland Publishing, 1978, p 313). Under normal non-inflammatory conditions neutrophil turnover takes place without harmful effects, despite the large bioaggressive and destructive potential of these cells displayed under various inflammatory conditions [Weiss S J: Tissue destruction by neutrophils. N Engl J Med 1989; 320:365-376]. A special mechanism of harmless neutrophil destruction is provided by apoptosis, genetically programmed cell suicide.

While apoptosis is a process used by the immune system in protecting the body, it is also used to maintain tolerance to self-antigens and therefore allowing the immune system to fulfill its role in distinguishing the body's own cells from foreign bodies.

Cellular apoptosis plays an important role in antigen-presentation. Immature dendritic cells have the capacity to engulf apoptotic cells and to acquire and immunologically present their antigens Immature dendritic cells that capture apoptotic macrophages exposed to killed influenza-virus, mature and activate lymphocytes to mount virus-specific CTL responses in the presence of conditioned media. However, in the absence of infection and conditioned media, immature dendritic cells do not mature following uptake of apoptotic cells and as a consequence are less able to efficiently present acquired antigens. Furthermore, it has been suggested that following interaction with apoptotic material, immature dendritic cells may have a role in maintaining peripheral tolerance to self-antigens that are permanently created at different sites. In support of this, autoimmunity or SLE-like disease has been observed in mice and humans deficient in receptors important for uptake of apoptotic cells such as ABC1 cassette transporter, Mer, and complement deficiencies, as further described hereinbelow. Clearance via specific receptors may dictate specific immune response or tolerance as demonstrated by TGF-beta and IL-10 secretion by macrophages following uptake of apoptotic cells by macrophages. Thus, cytokines, chemokines, eicosanoids, and additional mediators present in the milieu of the interaction, may polarize the immune response.

When the immune system is deficient in recognition between self- and non-self-antigens, the result is a state of disease, this may result in the immune system attacking one or more specific self molecules or cells leading to tissue and organ damage, resulting in autoimmune disease Immunopathology of non-targeted tissues also may be indirectly caused non-specifically as a consequence of inflammation resulting from immune rejection of neighboring cells and tissues. Other than classical autoimmune diseases such as those mentioned hereinabove, it is becoming increasingly apparent that many vascular disorders, including atherosclerotic forms of such disorders, have an autoimmune component, and a number of patients with vascular disease have circulating autoantibodies. Autoimmune diseases may be divided into two general types, namely systemic autoimmune diseases, such as SLE and scleroderma, and organ specific autoimmune diseases, such as multiple sclerosis, and diabetes. Many clinically different types and subtypes of autoimmune disease occur. Although each type of autoimmune disease is associated with a spectrum of clinical symptoms and aberrant laboratory parameters, signs and symptoms of autoimmune diseases frequently overlap so that one or more are diagnosed in the same patient. The vast majority cases in which one or more autoimmune disease has been diagnosed are characterized by the presence in the affected subject of antibodies directed against self-antigens, termed autoantibodies. Such autoantibodies are often present in tissues at ten to one hundred times the normal level in healthy individuals and give rise to a significant proportion of the organ and tissue damage associated with the particular autoimmune disease. For example, in the autoimmune disease myasthenia gravis, autoantibodies against a receptor in neuromuscular junction are associated with muscle weakness, while in SLE, anti-dsDNA antibodies are associated with nephritis in human patients and can cause nephritis upon injection to normal mice. In such diseases, the tissue and organ damage is attributed to the presence of autoantibodies and to the inflammation, which arises due inflammatory immune responses set off by autoantibodies.

Systemic lupus erythematosus is a model disease for understanding and developing inventive treatments for autoimmune disease in general. While it has long been appreciated that DNA and histones are major autoantigens SLE, only recently has evidence been provided that the DNA-histone complex, i.e., nucleosomes, are the preferred targets of autoantibodies in SLE. During apoptosis, the membrane of cells undergoing apoptosis form cytoplasmic blebs, some of which are shed as apoptotic bodies. It was recently demonstrated that exposure of keratinocytes to high frequency light induces apoptosis, and that the cell surface expression of the ribonucleoproteins Ro and La, but also of nucleosomes and ribosomes, can be explained by translocation of certain intracellular particles to the apoptotic surface blebs. Significantly, another translocation which occurs during apoptosis is that of phosphatidylserine (PS), an acidic phospholipid that normally resides on the inside of the cell, but flips to the outside of the cell membrane when the cell undergoes apoptosis. Phosphatidylserine, like cardiolipin, is a major autoantigen for anti-phospholipid antibodies in SLE. Taken together, these findings suggest that SLE involves autoimmunity directed against intracellular proteins translocated to the cell surface during apoptosis, and hence that SLE patients form an immune response to apoptotic material. This hypothesis is supported by the observation that brief, limited administration of syngeneic apoptotic cells to normal strains of mice leads to induction of autoantibodies and glomerular depositions. The immunopathology of SLE appears to further involve defective uptake of apoptotic material by macrophages, as observed in the reduced uptake/clearance of apoptotic cells by macrophages from SLE patients in-vitro, and by the high incidence of SLE in patients deficient in the C1q and C4 components of the complement system, which is involved in uptake of targeted antigens.

Lymphocytes, i.e. T-cells and B-cells, are relatively resistant to apoptosis. Upon antigenic stimulation, B-cells and T-cells proliferate and some will differentiate into effector cells. Plasma cells secrete antibodies that immobilize pathogens and promote their complement-mediated destruction and Fc (Ig constant region)-receptor-mediated ingestion by certain myeloid cells. Activated T-cells produce cytokines, some of which promote proliferation and functional activation of B-cells and T-cells themselves, whereas others provide feedback signals to cells of the innate immune system Immune effector mechanisms are highly potent weapons designed for the killing of free pathogens and also pathogen-infected host cells. This armory has the potential to destroy healthy cells and tissues because many of the effector molecules, such as pro-inflammatory cytokines, act in a non-antigen-specific manner and also because certain pathogen-specific receptors, such as B-cell receptors (BCRs) and T-cell receptors (TCRs) may cross-react with host antigens.

Immune responses to pathogens therefore pose a potential danger to the host and immunopathology occurs with many types of infection. In addition, chronically activated lymphocytes that are rapidly proliferating, particularly B-cells in germinal centers undergoing Ig-variable gene hyper-mutation, are at risk of sustaining mutations in proto-oncogenes or tumor suppressor genes that could lead to the development of lymphoma and/or leukaemia. Multiple regulatory mechanisms have evolved to prevent immunopathology. These include functional inactivation of cells of the immune system, a process that is potentially reversible and therefore does not eliminate the danger, and killing of no-longer needed and/or potentially dangerous cells by apoptosis [Marsden and A. Strasser, 2003. Annu. Rev. Immunol. 21:71-105].

Cells undergoing apoptosis signal neighboring cells, professional phagocytes, and/or antigen presenting cells to rapidly engulf them, without triggering an inflammatory or autoimmune response [10-12]. This process seems to play an important role in homeostasis, resolution of inflammation, and tolerance induction [13-15]. However disregulation of this process may represent a mechanism of escape from immune surveillance against infections and tumors and, if inefficient, it may support persistent inflammation and autoimmunity [16, 17].

Another issue that remains unclear is the role of apoptotic cell-derived antigens in cross-priming of immune responses. It has been shown that human dendritic cells, but not macrophages, efficiently present antigen that is derived from influenza-infected apoptotic monocytes, which stimulates class I-restricted CD8+ CTLs [18]. It remains unclear how dendritic cells derive a pro-inflammatory presentation of antigens from influenza, since these antigens are acquired from apoptotic cells that are usually considered anti-inflammatory, and that were shown to prevent maturation of dendritic cells [15, 19]. While in the former study conditioned media was employed as an adjuvant, the physiological adjuvants enabling cross-priming nevertheless remain unknown. Thus, antigens derived from apoptotic cells of given lineage may result in of activation or suppression of immunity due to mechanisms which remain to be resolved.

Manipulation of the immune system to treat immunopathology associated with autoimmune diseases, such as SLE, and transplantation-related diseases, such as GVHD, have been major goals of immunologists for many years. Traditionally, such manipulation has involved use of immunosuppressive drugs, such as corticosteroids, azathioprine, cyclophosphamide, and cyclosporine. While such drug-induced immunosuppression has resulted, for example, in improvement of the 5-year survival rate of SLE patients in the last three decades, it is far from being an ideal treatment since no cure is achieved, since such treatment is associated with very serious side-effects, including general immune suppression, leading to high rates of morbidity, and is the primary cause of premature mortality. Administration of biological agents such as anti-CD40 ligand, and CTLA-4Ig has also been advocated. However, the toxicity and efficacy of such treatments is suboptimal, being potentially associated, for example, with general immune suppression similarly to the above-mentioned immunosuppressive drugs.

Thus, in view of the tolerizing/non-inflammatory properties of dying leukocytes described hereinabove, a potentially optimal strategy for treatment of diseases characterized by pathological immune responses, such as autoimmune diseases and transplantation-related diseases, involves administration of dying leukocytes having immunosuppressive/non-inflammatory properties. Such a strategy would inherently circumvent the aforementioned significant disadvantages of prior art immunosuppressive drug-based treatment approaches.

Several prior art approaches involving administration of dying leukocytes have been employed or suggested for treatment of diseases characterized by pathological immune responses.

One approach suggests administration of apoptotic donor cells, such as apoptotic donor leukocytes, to facilitate engraftment of donor hematopoietic grafts transplanted into an allogeneic recipient [Penuche S. et al., 2004. Am J Transplant. 4:1361-5; Kleinclauss F. et al., 2003. Transplantation 75(9 Suppl):43S-45S]. Such an approach, however, suffers from various drawbacks, including requirement for administration of allogeneic leukocytes, which inherently are associated with risk of GVHD as well as of their own rejection, suboptimal efficacy, failure to demonstrate adequate safety with respect to potential for inflammatory side-effects, and/or of never having been attempted in human patients, and hence of never having demonstrated any therapeutic efficacy in human patients.

Another, apheresis-based, approach, termed "extracorporeal photopheresis", involves administering to a patient a photoactivatable pigment which can be specifically taken up by specific hematopoietic cells, such as T-cells, and following such uptake harvesting blood, isolating the specific hematopoietic cells, triggering their apoptosis via UV irradiation, and infusing them back into the patient (U.S. Pat. No. 6,219,584). This approach has been advocated for treatment of hypersensitivity, graft rejection, or SLE (U.S. Pat. No. 4,838,852); or for amelioration of GVHD. Prior art approaches involving apheresis, however, are often suboptimally effective, and may be associated with undesired side-effects of unknown origin, such as inflammatory side-effects (refer, for example, to: Siami G A. et al., 1997. Cryofiltration apheresis and plasma fractionation causing anaphylactoid reactions in patients receiving angiotensin converting enzyme inhibitors. Ther Apher. 1:325-9; Schwarzbeck A. et al., 1997. Anaphylactoid reactions during dextran apheresis may occur even in the absence of ACE-inhibitor administration. Nephrol Dial Transplant. 12:1083-4; Koga N. et al., 1993. Anaphylactoid reactions and bradykinin generation in patients treated with LDL-apheresis and an ACE inhibitor. ASAIO J. 39:M288-91; Strauss R G., 1996. Mechanisms of adverse effects during hemapheresis. J Clin Apheresis 11:160-4; Rossi P L. et al., 1991. Comparison of the side effects of therapeutic cytapheresis and those of other types of hemapheresis. Haematologica. 76 Suppl 1:75-80; Huestis D W., 1989. Risks and safety practices in hemapheresis procedures. Arch Pathol Lab Med. 113:273-8; Hocker P, Wagner A., 1987. Side-effects of cytapheresis with cell separators. Infusionsther Klin Ernahr 14 Suppl 4:31-5). Extracorporeal photopheresis, in particular, involves generation and administration of harmful necrotic/pro-inflammatory cells (Caricchio R. et al., 2003. Ultraviolet B Radiation-Induced Cell Death: Critical Role of Ultraviolet Dose in Inflammation and Lupus Autoantigen Redistribution. The Journal of Immunology 171:5778-5786).

Thus, all prior art approaches have failed to provide an adequate solution for using dying leukocytes for treatment of diseases characterized by pathological immune responses.

There is thus a widely recognized need for, and it would be highly advantageous to have, a disease treatment method devoid of the above limitation.

SUMMARY OF THE INVENTION

The present invention discloses the use of dying or dead leukocytes for treatment of diseases associated with pathological immune responses, and discloses devices for generating such dying or dead leukocytes. This use can be effected in a variety of ways, and these devices can be configured in a variety of ways, as further described and exemplified hereinbelow.

According to one aspect of the present invention there is provided a method of treating a disease characterized by a pathological immune response in a subject in need thereof, the method comprising administering to the subject a therapeutically effective amount of a cell preparation which comprises dying or dead leukocytes, the dying or dead leukocytes being capable of suppressing the pathological immune response, thereby treating the disease in the subject.

According to further features in preferred embodiments of the invention described below, the method further comprises subjecting live leukocytes to a cytocidal treatment selected from the group consisting of in-vitro serum deprivation, treatment with a steroid or steroid derivative, irradiation, and a pro-apoptotic treatment, thereby generating the dying or dead leukocytes.

According to still further features in the described preferred embodiments, the method of treating the disease further comprises inducing live leukocytes to adhere to a surface, thereby generating the dying or dead leukocytes.

According to still further features in the described preferred embodiments, the pathological immune response is directed against at least one antigen, and the dying or dead leukocytes comprise the at least one antigen.

According to still further features in the described preferred embodiments, the dying or dead leukocytes are derived from the subject.

According to still further features in the described preferred embodiments, the dying or dead leukocytes comprise dying or dead splenocytes and/or dying or dead thymocytes.

According to still further features in the described preferred embodiments, the dying or dead leukocytes comprise dying or dead lymphocytes.

According to still further features in the described preferred embodiments, the dying or dead leukocytes comprise dying or dead monocytes.

According to still further features in the described preferred embodiments, the dying or dead leukocytes comprise dying or dead neutrophils.

According to still further features in the described preferred embodiments, the dying or dead leukocytes comprise apoptotic leukocytes.

According to still further features in the described preferred embodiments, the disease is a systemic autoimmune disease.

According to still further features in the described preferred embodiments, the disease is an antibody-mediated autoimmune disease.

According to still further features in the described preferred embodiments, the disease is lupus erythematosus.

According to still further features in the described preferred embodiments, the disease is a transplantation-related disease.

According to still further features in the described preferred embodiments, the disease is graft-versus-host disease.

According to still further features in the described preferred embodiments, administering the cell preparation comprises administering to the subject a total number of the dying or dead leukocytes selected from a range of about 20 million to about 2 billion cells per kilogram body weight of the subject.

According to still further features in the described preferred embodiments, administering the cell preparation comprises administering to the subject at least one unit dose of the dying or dead leukocytes, wherein the unit dose comprises a number of the dying or dead leukocytes selected from a range of about 4 million to about 2 billion cells per kilogram body weight of the subject.

According to another aspect of the present invention there is provided a device for treating a disease characterized by a pathological immune response, the device comprising: (a) a pump for pumping blood from a subject into the device and returning blood to the subject from the device; (b) a leukocytes separator in communication with the pump for separating circulating leukocytes from whole blood; and (c) an apoptosis-inducing chamber or chambers in communication with the leukocytes separator for inducing apoptosis of the leukocytes to thereby obtain apoptotic leukocytes, and further in communication with the pump for administering the apoptotic leukocytes to the subject.

According to further features in preferred embodiments of the invention described below, the apoptosis-inducing chambers comprise a first chamber for inducing apoptosis of monocytes, a second chamber for inducing apoptosis of neutrophils, and a third chamber for inducing apoptosis of lymphocytes.

According to yet another aspect of the present invention there is provided a device for inducing apoptosis of leukocytes, wherein the device comprises an apoptosis-inducing chamber or chambers for inducing apoptosis of leukocytes to thereby obtain apoptotic leukocytes, wherein the apoptosis-inducing chamber or chambers is selected from the group consisting of a first chamber for inducing apoptosis of monocytes, a second chamber for inducing apoptosis of neutrophils, and a third chamber for inducing apoptosis of lymphocytes.

According to further features in preferred embodiments of the invention described below, the first chamber comprises a surface for enhancing adherence of monocytes thereto.

According to still further features in the described preferred embodiments, the device further comprises a first reservoir for containing a monocyte medium, wherein the monocyte medium is for inducing apoptosis of monocytes.

According to still further features in the described preferred embodiments, the device further comprises a second reservoir for containing a neutrophil medium, wherein the neutrophil medium is for inducing apoptosis of neutrophils.

According to still further features in the described preferred embodiments, the device further comprises a third reservoir for containing a lymphocyte medium, wherein the lymphocyte medium is for inducing apoptosis of lymphocytes.

According to still further features in the described preferred embodiments, the device further comprises a mechanism for resuspending surface-adherent monocytes.

According to still further features in the described preferred embodiments, the mechanism for resuspending the surface-adherent monocytes is selected from the group consisting of: a reservoir for containing a protease and a mechanism for introducing the protease into the first chamber; a flow-generating mechanism for generating in the first chamber a flow of sufficient force and direction for resuspending the surface-adherent monocytes; and a scraping mechanism for scraping the surface-adherent monocytes off the surface of the first chamber.

According to still further features in the described preferred embodiments, the apoptosis-inducing chamber or chambers comprises an apoptosis-inducing mechanism selected from the group consisting of: an irradiating mechanism for inducing apoptosis; a mechanical mechanism for inducing apoptosis; and a chemical or biochemical substance or environment for inducing apoptosis.

The present invention successfully addresses the shortcomings of the presently known configurations by providing a method of treating with improved safety and effectiveness diseases associated with pathological immune responses, such as autoimmune diseases and GVHD, by administration of dying or dead leukocytes, by providing a device for generating such leukocytes, and by providing a device for practicing such methods.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 5a-b are gene expression array analyses depicting de-novo transcription of pro-inflammatory cytokine/chemokine mRNAs by monocytes subjected to suspension+serum deprivation at 0 time and 30 minutes, respectively. Coordinates (A2, B2), which represent IL-1-beta and coordinates (E3, F3), representing IL-8, show no visible fluorescence at time zero and a marked fluorescence at 30 minutes following apoptosis induction. Some augmentation of basal levels is seen for cDNA of IL-6 (C3-D3) and IL-1-alpha (E1-F1). Other cDNAs that are present with viable cells and did not change much upon death induction are TGF-beta-1 (A7-B7), IL-2 (C2-D2), and TNF-alpha (A8-B8). MIF (E6-F6) shows downregulation. Other wells in this membrane that did not show fluorescence are (A1-B1) for G-CSF, (C1-D1) for GM-CSF, (E2-F2) for IL-4, (A3-B3) for IL-5, (A4-B4) for IL-10, (C4-D4) for IL-12-alpha (E4-F4) for IL-12-beta, (A5-B5) for IL-16, (C5-D5) for IL-17, (A6-B6) for LT-beta, (C6-D6) for MCP-1, (C7-D7) for TGF-beta-2, (E7-F7) for TGF-beta-3, and (C8-D8) for TNF-beta. Coordinates that represent negative controls are (G1-G2, PUC18); and as positive controls (G3-G4, beta-actin) and (G5-G6, G7-G8, E8-F8, GAPDH). Chemokine membrane screening showed only IL-8, MIP-1-alpha and MIP-1-beta upregulation (not shown). Membranes contained eotaxin, fractalkine, GROa/MGSA, HCC-4, MCP-3, SDF2, PF-4, MDC, HCC-1, I-309, I-TAC, lymphotactin, MCP-1, MCP-4, MIG, MIP-2, MIP-3-alpha, P10, SDF-1, RANTES. FIG. 5c is a data plot depicting representative cytokine and chemokine cDNA level changes as a function of time following induction of cell death. Note that only IL-1-beta, IL-8, and MIP-1-alpha are produced de-novo.

FIG. 8a is a photograph of a Western immunoblotting assay depicting that pro-inflammatory cytokine secretion during monocyte apoptosis is not NFkappaB-dependent. Shown is 37 kDa IkappaB and phosphorylated IkappaB (black arrow). Viable monocytes (lanes a and b), were incubated for 2 hours in the presence of 1 mg/ml zymosan with (lane a) or without (lane b) MG132 (a proteasome inhibitor). Monocytes undergoing apoptosis (lanes c and d) at 2 hours (lane c) and 10 minutes (lane d). As can be seen, viable monocytes exposed to zymosan show phosphorylation of IkappaB (lane b, black arrow) that does not appear in the presence of MG132 (lane a). No phosphorylation is seen at 10 minutes (lane d) or 2 hours (lane c) when monocytes undergo apoptosis. Additional samples at 5, 20, 30, 40, 60, and 90 minutes (not shown), following apoptosis induction did not show IkappaB phosphorylation (representative of 5 experiments). FIG. 8b is a bar-graph depicting that IL-1-beta secretion in the presence of MG132 is slightly elevated (3 experiments). FIG. 8c is a histogram depicting transcriptional activity in the presence of MG132 (representative of 3 experiments). Note that fold increases in the levels of mRNA (filled bars) are not changed in the presence of MG132 (empty bars).

FIG. 9a is a bar-graph depicting that after 24 hours in the presence of anti-Fas inhibitory antibodies (BD29 or ZB4), monocyte apoptosis was only slightly decreased (BD29 is shown) compared to the significant * (p<0.001) decrease in apoptosis seen in the presence of p38 inhibitor (p38INH) or p38 and anti-fas (ZB4). FIG. 9b is a Western immunoblotting assay depicting that P38 is expressed at comparable levels in monocytes exposed to LPS or induced to undergo apoptosis. FIG. 9c is a Western immunoblotting assay depicting that phosphorylated p38 is transiently increased upon LPS stimulation but shows sustained increase upon apoptosis. No phosphorylation of JNK was found (not shown). Representative of six experiments. FIG. 9d is a bar-graph depicting that IL-1-beta secretion by apoptotic monocytes is completely abrogated by specific p38 inhibitor (p38IN) but not in p38 control (DMSO). No inhibition is seen in the presence of JNK inhibitor (JNKIN) or its control (LTAT). FIG. 9e is a bar-graph depicting the marked decrease in IL-8 secretion from apoptotic monocytes in the presence of p38 inhibitor (p38IN) but not in control (DMSO) or JNK inhibitor (JNKIN).

DESCRIPTION OF THE PREFERRED EMBODIMENTS

Figure 1:
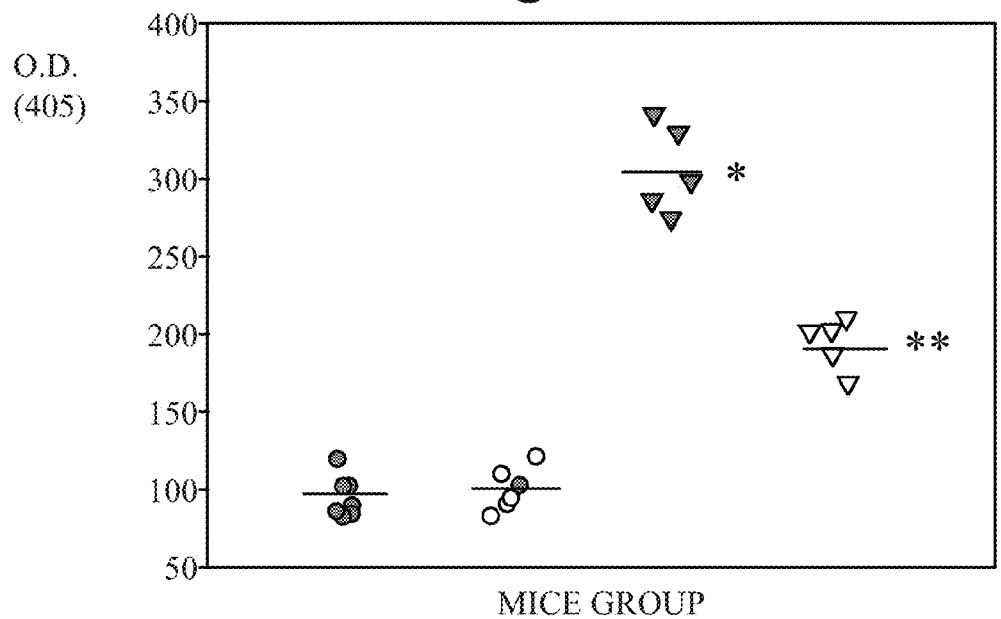
FIG. 1 is a histogram depicting reduction of serum anti-single-stranded DNA antibodies in MRL/MpJ-Fas$^{lpr}$ mice following treatment with syngeneic apoptotic cells. Filled circles, control group of 6 week-old MRL/lpr/lpr mice immunized with vehicle only; open circles, experimental group of 6 week-old MRL/lpr/lpr mice immunized with syngeneic apoptotic cells; filled triangles, control group after 10 weeks of treatment; open triangles, experimental group after 10 weeks of treatment.

The present invention is of methods of treating diseases associated with pathological immune responses using dying or dead leukocytes, of devices for generating such cells, and of devices for practicing such methods.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Various methods of using administration of dying leukocytes for treatment of diseases characterized by pathological immune responses have been described by the prior art.

One approach involves using administration of apoptotic allogeneic donor leukocytes, in an attempt to facilitate engraftment of allogeneic donor hematopoietic grafts [Penuche S. et al., 2004. Am J Transplant. 4:1361-5; Kleinclauss F. et al., 2003. Transplantation 75(9 Suppl):43S-45S]. Another, apheresis-based, approach for treatment of hypersensitivity, graft rejection, or systemic lupus erythematosus (U.S. Pat. No. 4,838,852); or for amelioration of GVHD, termed "extracorporeal photopheresis", involves administering to a patient a photoactivatable pigment which can be specifically taken up by specific hematopoietic cells, such as T-cells, and subsequently harvesting blood, isolating the specific hematopoietic cells, UV-irradiating the isolated cells, and re-infusing them into the patient (U.S. Pat. No. 6,219,584).

However, all such prior art approaches suffer from various drawbacks. For example, approaches involving administration of allogeneic leukocytes are associated with risk of GVHD and rejection of the administered leukocytes, and/or have never demonstrated any therapeutic efficacy in humans. Prior art approaches involving apheresis are often suboptimally effective, and may be associated with undesired and/or unexplained side-effects, such as inflammatory side-effects (refer, for example, to: Siami G A. et al., 1997. Cryofiltration apheresis and plasma fractionation causing anaphylactoid reactions in patients receiving angiotensin converting enzyme inhibitors. Ther Apher. 1:325-9; Schwarzbeck A. et al., 1997. Anaphylactoid reactions during dextran apheresis may occur even in the absence of ACE-inhibitor administration. Nephrol Dial Transplant. 12:1083-4; Koga N. et al., 1993. Anaphylactoid reactions and bradykinin generation in patients treated with LDL-apheresis and an ACE inhibitor. ASAIO J. 39:M288-91; Strauss R G., 1996. Mechanisms of adverse effects during hemapheresis. J Clin Apheresis 11:160-4; Rossi P L. et al., 1991. Comparison of the side effects of therapeutic cytapheresis and those of other types of hemapheresis. Haematologica. 76 Suppl 1:75-80; Huestis D W., 1989. Risks and safety practices in hemapheresis procedures. Arch Pathol Lab Med. 113:273-8; Hocker P, Wagner A., 1987. Side-effects of cytapheresis with cell separators. Infusionsther Klin Ernahr. 14 Suppl 4:31-5). Extracorporeal photopheresis, in particular, involves generation and administration of harmful necrotic/pro-inflammatory cells (Caricchio R. et al., 2003. Ultraviolet B Radiation-Induced Cell Death: Critical Role of Ultraviolet Dose in Inflammation and Lupus Autoantigen Redistribution. The Journal of Immunology 171:5778-5786).

Thus, the prior art fails to provide satisfactory methods of using administration dying leukocytes for treating diseases characterized by pathological immune responses.

While reducing the present invention to practice, as is described in Example 1 of the Examples section which follows, effective treatment of a systemic autoimmune disease in mammalian subjects by administration of autologous apoptotic lymphocytes was achieved for the first time relative to the prior art. As such, the present invention can be used to treat an autoimmune disease with no or minimal administration of harmful and suboptimally effective anti-inflammatory drugs, as is standard practice in the art. While further reducing the present invention to practice, as is described in Example 2 of the Examples section which follows, primary monocytes subjected to suspension conditions ex-vivo were found for the first time to undergo necrosis and to produce pro-inflammatory mediators, whereas, in sharp contrast, such cells subjected to substrate-adherent conditions were found for the first time to undergo apoptosis in the absence of production of pro-inflammatory mediators. As such, the present invention teaches for the first time that prior art procedures involving ex-vivo manipulation of blood, such as apheresis procedures, which inherently involve subjecting primary monocytes to suspension conditions, in fact involve induction of monocyte necrosis and concomitant secretion of pro-inflammatory mediators by such necrotic cells, and hence in fact involve introduction of potentially harmful pro-inflammatory mediators into recipients of therapeutic blood fractions obtained by apheresis. As described hereinabove, prior art apheresis procedures, which are employed in numerous therapeutic applications, including treatment of diseases associated with pathological immune responses, such as GVHD and autoimmune diseases, may be associated with suboptimal efficacy, and harmful side-effects, such as inflammatory side-effects. Thus, the present invention can be used to practice apheresis to as to produce blood fractions which are depleted of pro-inflammatory mediators relative to blood fractions produced via prior art apheresis methods. Therefore, the present invention can be used to treat, via apheresis-based methods, diseases associated with pathological immune responses, such as GVHD and autoimmune diseases, with improved safety and effectiveness relative to the prior art.

Thus, according to one aspect of the present invention there is provided a method of treating a disease characterized by a pathological immune response in a subject in need thereof. The method is effected by administering to the subject a therapeutically effective amount of a cell preparation which comprises dying or dead leukocytes which are capable of suppressing the pathological immune response.

The method of the present invention can be used to treat in any of various types of subject, any of various diseases associated with a pathological immune response. Such diseases particularly include autoimmune diseases, transplantation-related diseases, and inflammation-associated diseases. Examples of diseases characterized by pathological immune responses which can be effectively treated according to embodiments of the present invention are described hereinbelow.

As used herein, the term "treating" when relating to a disease of the present invention refers to preventing onset of the disease, alleviating, attenuating, palliating or eliminating the symptoms of a disease, slowing, reversing or arresting the progression of the disease, or curing the disease.

As used herein, the term "disease" refers to any medical disease, disorder, condition, or syndrome, or to any undesired and/or abnormal physiological morphological, cosmetic and/or physical state and/or condition.

Preferably, the method of the present invention is used to treat the disease in a mammalian subject, such as a human subject. It will be readily appreciated that the method can be used to treat a human subject in view of its successful use in treating a systemic autoimmune disease in mice, as is described and illustrated in Example 2 of the following Examples section, and in view of the well-established extensive and relevant homologies between the human and the murine immune systems.

While the dying or dead leukocytes (hereinafter referred to as "therapeutic leukocytes") may be dying or dead as a result of any of various types of suitable cell death processes, according to this aspect of the present invention, the therapeutic leukocytes are preferably undergoing apoptosis. Leukocytes undergoing apoptosis are referred to herein as "apoptotic" leukocytes.

Apoptosis, which is a distinct cell death process from necrosis, is the programmed and orderly physiological elimination of cells, occurring, for example, during normal cell and tissue development, T-lymphocyte killing of pathogen-infected cells, and self-elimination of mutationally damaged cells. Apoptotic cells are characterized by distinct morphologic alterations in the cytoplasm and nucleus, chromatin cleavage at regularly spaced sites, and endonucleolytic cleavage of genomic DNA at internucleosomal sites.

Necrosis, on the other hand, is an inherently pathological and pro-inflammatory process of cell death caused, typically but not exclusively, by the uncontrolled, progressive degradative action of enzymes following lethal cellular injury. Necrotic cells are typically characterized by mitochondrial swelling, nuclear flocculation, cell lysis, loss of membrane integrity, and ultimately cell death. Necrosis can be identified, by light, fluorescence or electron microscopy techniques, or via uptake of the dye trypan blue.

Without being bound to a paradigm, the present inventors are of the opinion that cell death may be suitably induced, as in apoptosis, so as to provide signals for suppressing immune responses, and that the method of the present invention harnesses such properties of processes to achieve effective treatment of a disease of the present invention by suppressing the pathological immune response associated therewith. In particular, still without being bound to a paradigm, the present inventors are of the opinion that therapeutic leukocytes of the present invention can suppress immune responses directed against antigens which are included in the therapeutic leukocytes. The aforementioned properties of apoptotic cells stand in sharp contrast to those of necrotic cells, since necrosis is inherently a pathological process that is associated with generation of pro-inflammatory "danger" signals serving to stimulate—as opposed to suppress—immune responses for the body's defense.

As used herein, the term "suppressing" when relating to an immune response, such as a pathological immune response of the present invention, refers to preventing or reducing the immune response.

Thus, according to teachings of the present invention, by virtue of providing non-antigen-specific immune suppressive signals, the method of the present invention can be used to treat diseases which are characterized by pathological non-antigen-specific immune responses, such as non-antigen-specific inflammation in general.

According to further teachings of the present invention, for treating a disease characterized by a pathological immune response which is directed against at least one antigen (referred to hereinafter as "targeted antigen"), the therapeutic leukocytes may advantageously include one or more of the targeted antigens. Thus, therapeutic leukocytes which include such targeted antigens, can be administered so as to suppress such a pathological immune response, to thereby achieve treatment of such a disease of the present invention.

While suitable therapeutic leukocytes which include targeted antigens are preferably derived from leukocytes selected endogenously expressing such targeted antigens, depending on the application and purpose, these may be alternately derived from leukocytes genetically modified to express such targeted antigens. It is well within the purview of the ordinarily skilled artisan to genetically modify leukocytes so as to induce these to include a polypeptide or nucleic acid targeted antigen. Ample guidance for genetically modifying leukocytes so as to induce such cells to include desired polypeptides or nucleic acids is provided in the literature of the art (refer, for example, to: Rossig C, Brenner M K., 2004. Genetic modification of T lymphocytes for adoptive immunotherapy. Mol Ther. 10:5-18; Grassmann R. et al., 1994. Viral transformation of human T lymphocytes. Adv Cancer Res. 63:211-44; Havemann K. et al., 2003. In-vitro transformation of monocytes and dendritic cells into endothelial like cells. Adv Exp Med Biol. 522:47-57; Mayne G C. et al., 2003. Centrifugation facilitates transduction of green fluorescent protein in human monocytes and macrophages by adenovirus at low multiplicity of infection. J Immunol Methods. 278:45-56).

The therapeutic leukocytes may have any one of various genotypes, depending on the application and purpose.

Preferably, for treating a disease characterized by pathological immune responses against antigens of the subject or a disease characterized by non-antigen-specific pathological immune responses, the therapeutic leukocytes are syngeneic with the subject, more preferably are derived from the subject. It will be appreciated that subject-derived/syngeneic leukocytes will be optimal for treating a disease characterized by immune responses directed against particular subject-specific variants, or a combination of variants, of targeted autoantigens (e.g. allelic, glycosylation, and/or splice variants of polypeptide autoantigens; or sequence variants of nucleic acid autoantigens; etc.), since such combinations may be highly specific to the individual.

In general, the use of syngeneic therapeutic leukocytes will avoid the risk of pro-inflammatory immune alloreactivity or xenoreactivity and concomitant stimulation of pathological immune responses inherent to the use of non-syngeneic therapeutic leukocytes, such as allogeneic or xenogeneic therapeutic leukocytes, respectively.

Alternately, the therapeutic leukocytes may be advantageously non-syngeneic with the subject, for example, where sufficient quantities of autologous therapeutic leukocytes are not available, or for treating a disease, such as allograft rejection, or alloimmune spontaneous abortion (Pandey M K. et al., 2004. Arch Gynecol Obstet. 269:161-72), involving pathological immune responses against allogeneic antigens from an allogeneic individual. According to the teachings of the present invention, in order to induce therapeutic immune tolerance in such diseases, the therapeutic leukocytes are preferably derived from the allogeneic individual, i.e. the graft donor or the father of the fetus for treatment of allograft rejection or alloimmune spontaneous abortion, respectively.

Preferably, non-syngeneic therapeutic leukocytes are allogeneic leukocytes, most preferably allogeneic leukocytes which are haplotype-matched with the subject. Haplotype-matching of human subjects with allogeneic cells is routinely practiced in the art in the context of therapeutic transplantation, and usually involves matching of HLA-A, HLA-B, and HLA-DR alleles.

The therapeutic leukocytes used to practice the method of the present invention may be derived from leukocytes of any one of various lineages, depending on the application and purpose.

According to a most preferred embodiment, the therapeutic leukocytes are dying or dead lymphocytes (referred to hereinafter as "therapeutic lymphocytes").

As is further described hereinbelow, and as is described and illustrated in Examples 1 of the Examples section which follows therapeutic lymphocytes can be used according to the present teachings to effectively treat, without or with minimal requirement for harmful prior art administration of toxic immunosuppressive agents, a disease characterized by a pathological immune response, such as an autoimmune disease, such as a systemic autoimmune disease, such as systemic lupus erythematosus.

According to a preferred embodiment, the therapeutic leukocytes are dying or dead monocytes (referred to hereinafter as "therapeutic monocytes").

On the basis of the novel and unexpected experimental results set forth in Example 2 of the following Examples section, and as is further described hereinbelow, the method of the present invention can employ administration of a cell preparation comprising therapeutic monocytes to treat with enhanced safety and effectiveness relative to the prior art a disease of the present invention which is amenable to treatment by administration of dying or dead cells generated via an apheresis procedure involving suspension of monocytes.

As used herein, the phrase "suspension conditions" refers to any culturing conditions which do not involve adhesion of cultured cells to a surface, such as static culturing conditions in a culture recipient having an underlying substrate with a non-cell adherent surface (e.g. non-tissue culture-treated petri dishes), or dynamic culturing conditions, such as those involving shaking, which do not allow for static contact of cultured cells with a surface/substrate.

According to another embodiment, the therapeutic leukocytes are dying or dead neutrophils (referred to hereinafter as "therapeutic neutrophils").

As is further described hereinbelow, and therapeutic neutrophils can be used according to the present teachings to effectively treat, any of various diseases which are associated with a pathological immune response.

Alternately, the therapeutic leukocytes used to practice the method of the present invention may be derived from any lineage, or sub-lineage, of nucleated cells of the immune system and/or hematopoietic system, including but not limited to dendritic cells, macrophages, mast cells, basophils, hematopoietic stem cells, bone marrow cells, natural killer cells, and the like.

Leukocytes from which therapeutic leukocytes of the present invention may be derived (referred to hereinafter as "source leukocytes") may be obtained in any of various suitable ways, from any of various suitable anatomical compartments, according to any of various commonly practiced methods, depending on the application and purpose, desired leukocyte lineage, etc.

Preferably, the source leukocytes are primary leukocytes, more preferably primary peripheral blood leukocytes.

Primary lymphocytes, monocytes and neutrophils may be most conveniently derived from peripheral blood. Peripheral blood leukocytes include 60 percent neutrophils, 30 percent lymphocytes, and 7 percent monocytes.

It will be well within the purview of the ordinarily skilled artisan to obtain specific types of source leukocytes from blood, according to routinely practiced methods. Obtaining source lymphocytes, monocytes and/or neutrophils, can be achieved, for example, by harvesting blood in the presence of an anticoagulant, such as heparin or citrate. The harvested blood is then centrifuged over a Ficoll cushion to isolate lymphocytes and monocytes at the gradient interface, and neutrophils and erythrocytes in the pellet. Leukocytes may be separated from each other via standard immunomagnetic selection or immunofluorescent flow cytometry techniques according to their specific surface markers, or via centrifugal elutriation. For example, monocytes can be selected as the CD14+ fraction, T-lymphocytes can be selected as CD3+ fraction, B-lymphocytes can be selected as the CD19+ or CD22+ fraction, and neutrophils can be selected as the CD15+ fraction. Lymphocytes and monocytes may be isolated from each other by subjecting these cells to substrate-adherent conditions, such as by static culture in a tissue culture-treated culturing recipient, which results in selective adherence of the monocytes, but not the lymphocytes, to the cell-adherent substrate. Neutrophils may be isolated from other blood cells via standard counterflow centrifugal elutriation protocols.

Isolation of source monocytes is preferably performed via immunomagnetic or substrate-adherence-based selection, according to the protocols provided in the Materials and Methods section of Example 2 of the Examples section which follows.

Therapeutic lymphocytes may suitably be derived from lymphoid tissues, such as spleen, or thymus. As is described in Example 1 of the Examples section below, therapeutic leukocytes derived from source splenocytes or thymocytes may be used according to the present teachings to effectively treat a disease of the present invention, such as an autoimmune disease, such as a systemic autoimmune disease, such as systemic lupus erythematosus.

In cases where suitable primary source leukocytes are unavailable, or are not available in sufficient quantities, the therapeutic leukocytes may be derived from cultured primary source leukocytes, or may be derived from suitable established cell lines.

One of ordinary skill in the art will possess the necessary expertise to suitably culture primary leukocytes so as to generate desired quantities of cultured source leukocytes of the present invention, and ample guidance for practicing such culturing methods is available in the literature of the art (refer, for example, to: Bonnard G D., 1981. Long-term cultures of immunocompetent T lymphocytes. Prog Clin Biol Res. 58:45-56; Baron C L. et al., 1999. Two distinct cell populations are obtained from human blood monocytes cultured with M-CSF, GM-CSF and IL-4. Eur J Cancer. 35:539-40; McGee Z A. et al., 1989. The use of neutrophils, macrophages and organ cultures to assess the penetration of human cells by antimicrobials. Prog Drug Res. 33:83-92). Culturing of suitable source leukocytes, such as leukocytes of human origin, may be performed in-vivo, for example in immune deficient hosts, such as in lines of severe combined immunodeficiency (SCID) animals.

One of ordinary skill in the art will further possess the necessary expertise to establish, purchase, or otherwise obtain suitable established leukocyte cell lines from which to derive the therapeutic leukocytes. Suitable leukocyte cell lines may be obtained from commercial suppliers, such as the American Tissue Type Collection (ATCC). Established leukocyte cell lines may be particularly amenable to genetic modification, for example, to thereby include an antigen targeted by a pathological immune response of a disease of the present invention, as described hereinabove, for treatment of a disease of the present invention characterized by a pathological immune response targeted against such an antigen.

It will be evident to the ordinarily skilled artisan that source leukocytes should not be obtained via a technique which will significantly interfere with their capacity to produce the therapeutic leukocytes.

Source leukocytes may treated in any of various ways, in accordance with known prior art methods, so as to produce the therapeutic leukocytes, depending on the application and purpose.

Apoptosis of leukocytes may be induced according to a wide variety of treatments which are well known and commonly practiced in the art. Such treatments include, but are not limited to: culturing under conditions of growth factor and/or nutrient deprivation; culturing under conditions of cellular substrate-adherence; culturing under conditions of serum-withdrawal; irradiation, for example with UV or gamma rays; treatment with a biological apoptosis-inducing mediator, such as an activating death receptor ligand such as perforin; treatment with apoptosis-inducing cells, such as immunoreactive cytotoxic T-lymphocytes (CTLs); treatment with immunosuppressive drugs such as steroids, corticosteroids, dexamethasone, cyclophosphamide, methotrexate, azathioprine, cyclosporine, staurosporine, and the like; cryotreatment; hyperthermal treatment; culturing under cytotoxically acidic conditions; culturing under cytotoxically alkaline conditions; culturing under cytotoxically hyperosmolar conditions; culturing under cytotoxically hypoosmolar conditions; culturing under cytotoxically oxidizing conditions, for example in the presence of cytotoxically high concentrations of oxidants, such as hydrogen peroxide; etc. Preferably apoptosis of lymphocytes, such as primary lymphocytes, so as to generate therapeutic lymphocytes of the present invention is induced by treating the primary lymphocytes with serum deprivation, a corticosteroid, or irradiation. Preferably, inducing apoptosis of primary lymphocytes via treatment with a corticosteroid is effected by treating the primary lymphocytes with dexamethasone, more preferably with dexamethasone at a concentration of about 1 micromolar. Preferably, inducing apoptosis of primary lymphocytes via irradiation is effected by treating the primary lymphocytes with gamma-irradiation, more preferably with a dosage of about 66 rad. As is described and illustrated in Example 1 of the Examples section below subjecting primary lymphocytes to such preferred apoptosis-inducing treatments can be used to generate therapeutic leukocytes which may be used according to the present teachings to effectively treat a disease of the present invention, such as an autoimmune disease, such as a systemic autoimmune disease, such systemic lupus erythematosus.

As used herein the term "about" refers to plus/minus 10 percent.

Preferably, apoptosis of monocytes, such as primary monocytes, so as to generate therapeutic monocytes of the present invention is induced by subjecting the monocytes to in-vitro conditions of substrate/surface-adherence, as is taught for the first time in the present specification, more preferably concomitantly under conditions of serum deprivation. Subjecting the monocytes to in-vitro substrate/surface-adherent conditions suitable to produce therapeutic monocytes of the present invention may be suitably effected, for example, by culturing primary monocytes in tissue culture-coated tissue culture flasks under conditions of serum deprivation for a period of 40 minutes. As is described and illustrated in Example 2 of the Examples section below, such treatment will generate non-pro-inflammatory apoptotic monocytes suitable for practicing the method of the present invention.

The presently disclosed finding that monocytes undergo necrosis upon suspension is clearly novel and highly unexpected since the art would lead one of ordinary skill in the art to expect the opposite, namely that monocytes upon losing substrate adherence would undergo apoptosis (refer, for example, to Hamada K. et al., 1998. Biochem Biophys Res Commun. 244:745-50).

Any of various types of cell-adherent surfaces/substrates, as further described hereinbelow, may be employed for inducing monocyte apoptosis. Adherent leukocytes, such as adherent monocytes, may be released from a surface by treatment with a combination of exposure to a compound (referred to hereinafter as "cell-releasing compound") capable of facilitating release of surface-adherent cells, such as surface-adherent monocytes, and application of fluid shear flow or scraping with a suitable instrument, such as a rubber policeman, serving to release the adherent cells from the surface. Such suitable cell-releasing compounds, and appropriate methods of their use (compound concentration, duration of exposure to compound, termination of exposure of compound, etc.), are well known and widely employed in the art. Such compounds include, for example, proteases, such as trypsin; and divalent cation chelators, such as EDTA. It will be appreciated that methods of releasing adherent cells which would normally harm or disrupt viable cells may be employed since the cells are already apoptotic and do not necessarily need to be administered as intact cell structures so as to enable disease treatment according to the method of the present invention.

Apoptosis of source leukocytes so as to generate the therapeutic leukocytes is preferably effected in-vitro. When using primary leukocytes as source leukocytes, apoptosis of the source leukocytes is preferably effected outside the body, i.e. ex-vivo. Alternately, apoptosis of source leukocytes may be induced in-vivo/in-situ.

Apoptosis of a cell, such as therapeutic leukocyte of the present invention, can be confirmed by any of various commonly employed methods. Such methods include gel electrophoresis of cellular DNA to detect apoptosis-specific ladder-like DNA fragment patterns, TUNEL-staining to detect apoptosis-specific DNA fragmentation, staining with an annexin-fluorophore conjugate to detect apoptosis-specific reversal of cell membrane orientation, staining with anti-cleaved caspase-3 antibody for detection of apoptosis-specific caspase activation, microscopic inspection to detect apoptosis-specific cellular fragmentation and blebbing, and the like.

As is described and illustrated in Example 2 of the Examples section below, primary monocytes were induced to undergo apoptosis by incubation in a tissue culture dish having a cell-adherent substrate. As such, the present inventors have devised and implemented a novel device for inducing apoptosis of source leukocytes in-vitro.

Figure 10:
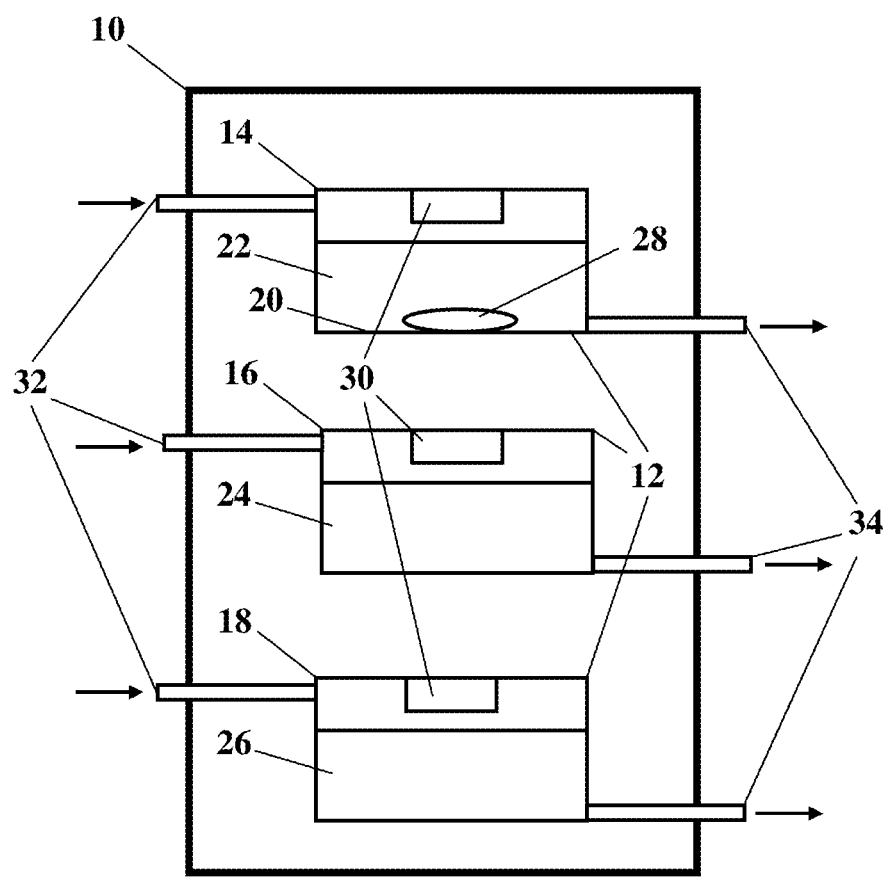
FIG. 10 is a schematic diagram depicting a device for inducing apoptosis of leukocytes. Arrows indicate direction of fluid flow.

Thus, according to another aspect the present invention there is provided an apoptosis-inducing device for inducing apoptosis of leukocytes (FIG. 10). The device 10 comprises an apoptosis-inducing chamber or chambers (each indicated by 12) selected from a chamber 14 for inducing apoptosis of monocytes (referred to hereinafter as "monocyte chamber"), a chamber 16 for inducing apoptosis of neutrophils (referred to hereinafter as "neutrophil chamber"), and/or a chamber 18 for inducing apoptosis of lymphocytes (referred to hereinafter as "lymphocyte chamber").

The device may comprise any of various combinations of apoptosis-inducing chambers, depending on which lineages of apoptotic leukocytes are desired.

In order to facilitate apoptosis of monocytes, the monocyte chamber preferably comprises a surface 20 for enhancing adherence of monocytes thereto, a reservoir 22 for containing a medium for inducing apoptosis of monocytes (referred to hereinafter as "monocyte medium"), and/or a mechanism 28 for resuspending surface-adherent monocytes (referred to hereinafter as "cell-adherent surface"), more preferably all of which.

Preferably, the cell-adherent surface is hydrophilic and negatively charged, and may be obtained in any of various ways known in the art, preferably by modifying a polystyrene surface using, for example, corona discharge, or gas-plasma. These processes generate highly energetic oxygen ions which graft onto the surface polystyrene chains so that the surface becomes hydrophilic and negatively charged, thereby facilitating cellular adherence thereto. Suitable cell-adherent surfaces for inducing leukocyte apoptosis according to the present invention may be provided by any one of various tissue-culture-treated tissue culture recipients designed for facilitating cell-adherence thereto which are available from various commercial suppliers (e.g. Corning, Perkin-Elmer, Fisher Scientific, Evergreen Scientific, Nunc, etc.).

The monocyte chamber may comprise any of various suitable mechanisms for resuspending surface-adherent monocytes, so as to enable the harvesting thereof. Suitable mechanisms for such purpose include any combination of: a reservoir for containing a cell-releasing compound of the present invention, and a mechanism for introducing the cell-releasing compound into the monocyte chamber; a flow-generating mechanism for generating in the monocyte chamber a flow of sufficient force and direction for resuspending the surface-adherent monocytes, and a mechanism of controlling the operation of the flow-generating mechanism; and a scraping mechanism for scraping the surface-adherent monocytes off the cell-adherent surface of the monocyte chamber, and a mechanism for controlling the operation of the scraping mechanism.

Suitable flow-generating mechanisms for facilitating resuspension of surface-adherent cells, such as surface-adherent monocytes, include for example, magnetic stirrers, and fluid mixing mechanisms based on rotating propeller blades.

A suitable scraping mechanism for scraping the surface-adherent monocytes off the cell-adherent surface of the monocyte chamber is an automated rubber policeman.

Preferably, the neutrophil chamber comprises a reservoir 24 for containing a medium for inducing apoptosis of neutrophils (referred to hereinafter as "neutrophil medium").

Preferably, the lymphocyte chamber comprises a reservoir 26 for containing a medium for inducing apoptosis of lymphocytes (referred to hereinafter as "lymphocyte medium").

Depending on the application and purpose, each apoptosis-inducing chamber may be configured so as to comprise an apoptosis-inducing mechanism 30 selected from the group consisting of: an irradiating mechanism for inducing apoptosis, a mechanical mechanism for inducing apoptosis, and a chemical or biochemical substance or environment for inducing apoptosis.

Preferably, in order to optimally control induction of apoptosis of leukocytes and their maintenance at all stages, each apoptosis inducing chamber is preferably equipped with a temperature control mechanism enabling maintenance of leukocytes at a desired temperature, and is further preferably equipped with a mechanism for maintenance of carbon dioxide air levels appropriate to the particular cell medium employed.

In order to enable addition of fluids, such as a suspension of source leukocytes to the apoptosis-inducing chambers; and removal of a fluid, such as a suspension of therapeutic leukocytes therefrom; each apoptosis-inducing chamber is preferably equipped with a fluid inlet 32 and a valve for controlling fluid flow therethrough, and a fluid outlet 34 and a valve for controlling fluid flow therethrough.

Thus, the device according to this aspect of the present invention is configured so as to enable introduction of each lymphocytes, monocytes, and/or neutrophils into respective chambers configured so as to induce apoptosis thereof according to the teachings of the present invention, and is configured so as to enable harvesting of such leukocytes from such chambers for administration for disease treatment according to the method of the present invention.

Treatment of a disease characterized by a pathological immune response according to the method of the present invention may be effectively practiced, depending on the application and purpose, by administering to the subject according to any of various suitable administration regimens a therapeutically effective amount of any of various suitable types of cell preparation which comprise therapeutic leukocytes of the present invention.

In particular, depending on the application and purpose, disease treatment may be effectively practiced by administering to the subject a therapeutically effective amount of a cell preparation which may comprise any of various combinations of therapeutic leukocyte lineages.

Examples of specific treatment protocols which may be used for treatment of various diseases via administration of therapeutic lymphocytes, therapeutic monocytes, and/or therapeutic neutrophils of the present invention are provided in Examples 3, 4 and 5 of the Examples section which follows, respectively.

According to a preferred embodiment, administration of therapeutic lymphocytes is used to treat an autoimmune disease. Preferably, the autoimmune disease is a systemic autoimmune disease, more preferably systemic lupus erythematosus.

According to another embodiment, administration of combined therapeutic lymphocytes, monocytes, and neutrophils may be used to treat graft-versus-host disease.

According to a preferred embodiment of the present invention, treatment of a disease of the present invention is effected by administering to the subject a cell preparation which comprises a total dose of about 200 million therapeutic leukocytes per kilogram body weight. Preferably, such a total dose is administered as unit doses of about 40 million cells per kilogram body weight, and/or is administered as unit doses at weekly intervals, more preferably both of which. Suitable total doses according to this embodiment include total doses of about 20 million to about 2 billion cells per kilogram body weight, more preferably about 40 million to about 1 billion cells per kilogram body weight, more preferably about 80 million to about 500 million cells per kilogram body weight, and more preferably about 160 million to about 250 million cells per kilogram body weight. Suitable unit doses according to this embodiment include unit doses of about 4 million to about 400 million cells per kilogram body weight, more preferably about 8 million to about 200 million cells per kilogram body weight, more preferably about 16 million to about 100 million cells per kilogram body weight, and more preferably about 32 million to about 50 million cells per kilogram body weight.

Preferably, the therapeutic leukocytes are administered to the subject systemically, more preferably via the intravenous route. Alternately, the therapeutic leukocytes may be administered to the subject according to any of various other routes, including, but not limited to, the parenteral, intraperitoneal, intramuscular, subcutaneous, oral, transnasal and rectal routes.

Preferably, the therapeutic leukocytes are administered to the subject suspended in a suitable physiological buffer, such as saline solution, PBS, HBSS, and the like.

As is described and illustrated in Example 1 of the Examples section which follows, a disease of the present invention (systemic lupus erythematosus) was effectively treated in a mouse (average weight 0.025 kilograms) by intravenous administration of 5 doses of one million therapeutic lymphocytes at weekly intervals, which corresponds to the aforementioned preferred total and unit doses of 200 million and 40 million cells per kilogram body weight, respectively.

Depending on the application and purpose, disease treatment may be advantageously effected according to the teachings of the present invention in conjunction with standard prior art therapies, and/or by co-administration of an immunosuppressive molecule, such as IL-10 or TGF-beta.

During and after disease treatment according to the method of the present invention, disease status will preferably be closely monitored so as to optimize and suitably modify the treatment. For example, levels of any of various pro-inflammatory cytokines, chemokines or other molecules may be monitored in the patient to facilitate monitoring of disease treatment. In the case of autoimmune diseases, tissue levels of relevant autoantibodies may be measured for monitoring disease treatment. For example, in the case a systemic autoimmune disease, such as systemic lupus erythematosus, such autoantibodies include those specific for double-stranded DNA, and those specific for phospholipids.

One of ordinary skill in the art, such as a physician, preferably a specialist in the disease to be treated, will possess the necessary expertise for applying the teachings of the present invention so as to effectively treat a disease of the present invention in a human subject.

While conceiving the present invention, the present inventors have devised a novel disease treatment device which can harvest blood from the subject, generate desired therapeutic leukocytes from the harvested blood, and re-infuse the therapeutic leukocytes to the subject.

Figure 11:
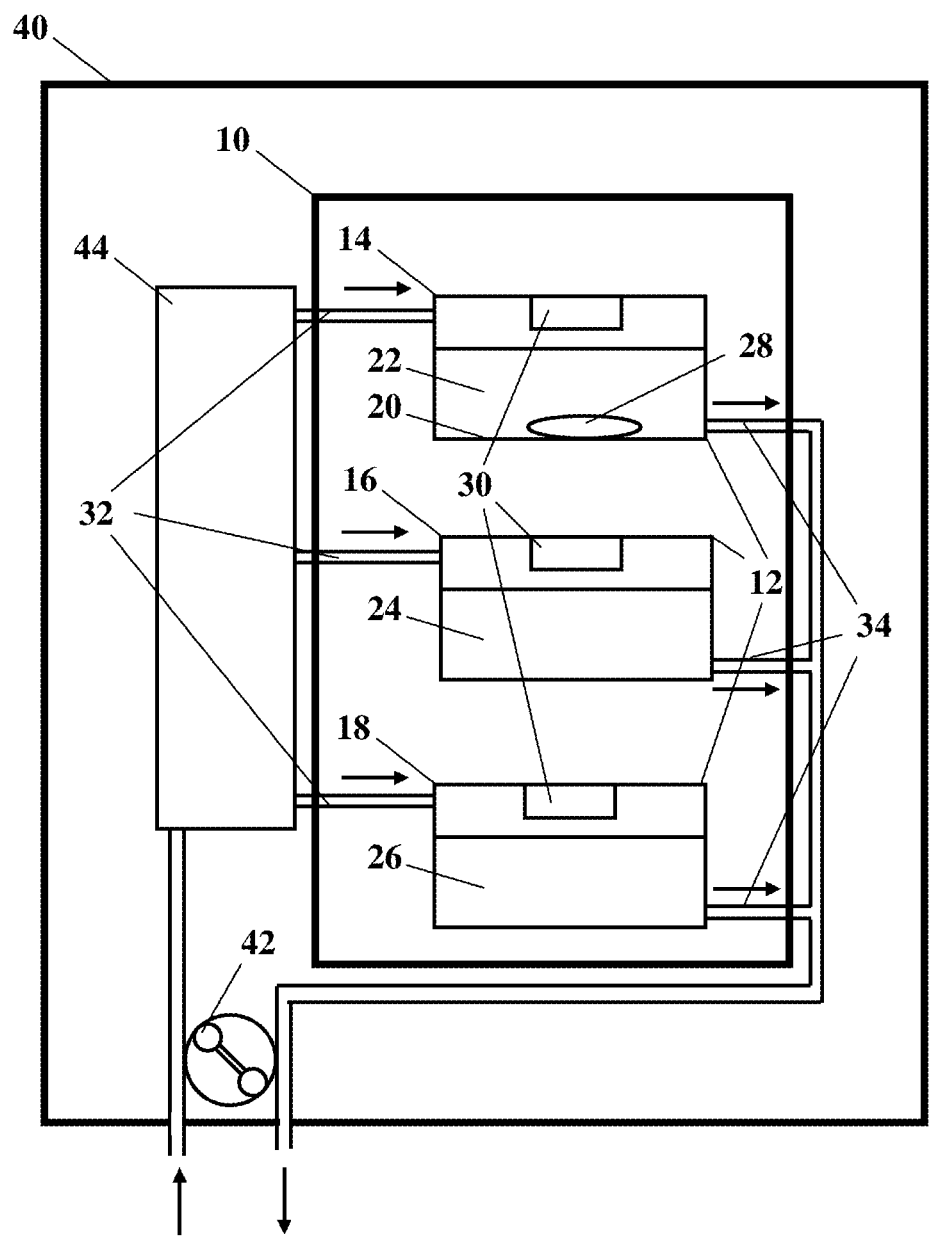
FIG. 11 is a schematic diagram depicting a device for treating a disease characterized by a pathological immune response. Arrows indicate direction of fluid flow.

Thus, according to a further aspect of the present invention, there is provided a disease treatment device, an example of which is shown in FIG. 11.

The disease-treatment device 40 comprises a pump 42 for pumping blood from a subject into the device and returning blood to the subject from the device; a leukocytes separator 44 in communication with the pump for separating circulating leukocytes from whole blood; and the apoptosis-inducing device 10 of the present invention in communication with the leukocytes separator for inducing apoptosis of the leukocytes, and further in communication with the pump for administering the apoptotic leukocytes to the subject.

The disease-treatment device of the present invention is configured essentially as a prior art blood cell apheresis device capable of harvesting blood from a subject, isolating blood cells, subjecting the isolated cells to a given treatment, and re-infusing the treated cells back into the subject. Such prior art devices are widely used, for example, for practicing CD34+ cell leukapheresis, or leukocyte photopheresis. The disease-treatment device of the present invention comprises the novel and inventive feature of including the apoptosis-inducing device of the present invention for inducing apoptosis, in accordance with the method of the present invention, of separated leukocytes prior to their re-infusion into the subject. As such, it will be well within the purvey of one of ordinary skill in the art, in view of prior art technology and the present teachings, to assemble and use the disease-treatment device of the present invention for effectively treating a disease associated with a pathological immune response in accordance with the method of the present invention. For example, it will be well within the purview of one of ordinary skill in the art to employ prior art apheresis-specific blood harvesting and re-infusion technology to achieve pumping of blood from the subject into the disease treatment device and back into the subject. It will also be well within the purview of one of ordinary skill in the art to employ prior art apheresis-specific cell separation technology, such as centrifugal and/or immunoadsorption-based technology, to achieve isolation of desired source leukocytes.

Ample general guidance relating to leukocyte apheresis devices, such as the disease-treatment device of the present invention, and their use, is provided in the literature of the art (refer, for example, to: Burgstaler E A. et al., 2004.

Hematopoietic progenitor cell large volume leukapheresis (LVL) on the Fenwal Amicus blood separator. J Clin Apheresis. 19:103-11; Schwella N. et al., 2003. Comparison of two leukapheresis programs for computerized collection of blood progenitor cells on a new cell separator. Transfusion. 43(1):58-64; Kohgo Y. et al., 2002. Leukocyte apheresis using a centrifugal cell separator in refractory ulcerative colitis: a multicenter open label trial. Ther Apher. 6:255-60; Accorsi P. et al., 2001. Large volume leukapheresis with AMICUS cell separator in peripheral blood stem cell autologous transplant. Transfus Apheresis Sci. 24:79-83; Sueoka A., 1997. Present status of apheresis technologies: Part 1. Membrane plasma separator. Ther Apher. 1:42-8; Wooten S L. et al., 1991. Control and optimization of apheresis procedures in a COBE 2997 cell separator. J Biomech Eng. 113:11-20; Del Monte C. et al., 1990. Collection of peripheral blood stem cells by apheresis with continuous flow blood cell separator Dideco Vivacell. Haematologica. 75 Suppl 1:18-21).

Ample guidance specifically relating to lymphocyte apheresis devices and techniques is provided in the literature of the art (refer, for example, to: Zic J A., 2003. The treatment of cutaneous T-cell lymphoma with photopheresis. Dermatol Ther. 16:337-46; Foss F M. et al., 2002. Extracorporeal photopheresis in chronic graft-versus-host disease. Bone Marrow Transplant. 29:719-25; Oliven A, Shechter Y., 2001. Extracorporeal photopheresis: a review. Blood Rev. 15:103-8; Rook A H. et al., 1999. Photopheresis: clinical applications and mechanism of action. J Investig Dermatol Symp Proc. 4:85-90).

Ample guidance specifically relating to monocyte apheresis devices and techniques is provided in the literature of the art (refer, for example, to: Wagner S J. et al., 2005. Monocyte enrichment of mononuclear apheresis preparations with a multistep back-flush procedure on a cord blood filter. Transfusion. 45:433-9).

Ample guidance specifically relating to neutrophil apheresis devices and techniques is provided in the literature of the art (refer, for example, to: Wright D G, Klock J C., 1979. Functional changes in neutrophils collected by filtration leukapheresis and their relationship to cellular events that occur during adherence of neutrophils to nylon fibers. Exp Hematol. 7(4 Suppl):11-23; McCullough J., 1979. Leukapheresis and granulocyte transfusion. CRC Crit Rev Clin Lab Sci. 10:275-327).

The disease-treatment device of the present invention presents various advantages over prior art apheresis devices used for disease treatment. The device particularly enables practicing of photopheresis for treatment of diseases characterized by pathological immune responses with greater safety and effectiveness relative to the prior art since it avoids generation of pro-inflammatory leukocyte necrosis inherent to prior art devices, by virtue of enabling non-pro-inflammatory leukocyte apoptosis, such as monocyte and neutrophil apoptosis.

Examples of therapeutic applications of the disease-treatment device of the present invention are described in Examples 3, 4, and 5 of the Examples section which follows.

Embodiments of the present invention can be used to treat any of various diseases characterized by a pathological immune response.

Preferably, the disease is an autoimmune disease or a transplantation-related disease.

Preferably, the autoimmune disease is a systemic autoimmune disease and/or an antibody-mediated autoimmune disease. Most preferably, the autoimmune disease is systemic lupus erythematosus (SLE).

Preferably, the transplantation-related disease is graft-versus-host disease (GVHD).

The disease characterized by a pathological immune response may be any of various inflammatory/inflammation-associated diseases.

The present invention can be used to treat a disease which is characterized by a pathological immune response in any of various anatomical compartments of the body.

Specific examples of diseases characterized by pathological immune responses according to the present invention are listed hereinbelow, and are described in Examples 3, 4, and 5 of the following Examples section.

Examples of antibody-mediated autoimmune diseases include but are not limited to rheumatoid diseases, rheumatoid autoimmune diseases, rheumatoid arthritis (Krenn V. et al., Histol Histopathol 2000 July; 15 (3):791), spondylitis, ankylosing spondylitis (Jan Voswinkel et al., Arthritis Res 2001; 3 (3): 189), systemic diseases, systemic autoimmune diseases, systemic lupus erythematosus (Erikson J. et al., Immunol Res 1998; 17 (1-2):49), sclerosis, systemic sclerosis (Renaudineau Y. et al., Clin Diagn Lab Immunol. 1999 March; 6 (2):156); Chan O T. et al., Immunol Rev 1999 June; 169:107), glandular diseases, glandular autoimmune diseases, pancreatic autoimmune diseases, diabetes, Type I diabetes (Zimmet P. Diabetes Res Clin Pract 1996 October; 34 Suppl:S125), thyroid diseases, autoimmune thyroid diseases, Graves' disease (Orgiazzi J. Endocrinol Metab Clin North Am 2000 June; 29 (2):339), thyroiditis, spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), myxedema, idiopathic myxedema (Mitsuma T. Nippon Rinsho. 1999 August; 57 (8):1759); autoimmune reproductive diseases, ovarian diseases, ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), repeated fetal loss (Tincani A. et al., Lupus 1998; 7 Suppl 2:S107-9), neurodegenerative diseases, neurological diseases, neurological autoimmune diseases, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83), motor neuropathies (Kornberg A J. J Clin Neurosci. 2000 May; 7 (3):191), Guillain-Bane syndrome, neuropathies and autoimmune neuropathies (Kusunoki S. Am J Med Sci. 2000 April; 319 (4):234), myasthenic diseases, Lambert-Eaton myasthenic syndrome (Takamori M. Am J Med Sci. 2000 April; 319 (4):204), paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydeham chorea, Gilles de la Tourette syndrome, polyendocrinopathies, autoimmune polyendocrinopathies (Antoine J C. and Honnorat J. Rev Neurol (Paris) 2000 January; 156 (1):23); neuropathies, dysimmune neuropathies (Nobile-Orazio E. et al., Electroencephalogr Clin Neurophysiol Suppl 1999; 50:419); neuromyotonia, acquired neuromyotonia, arthrogryposis multiplex congenita (Vincent A. et al., Ann N Y Acad Sci. 1998 May 13; 841:482), cardiovascular diseases, cardiovascular autoimmune diseases, atherosclerosis (Matsuura E. et al., Lupus. 1998; 7 Suppl 2:5135), myocardial infarction (Vaarala O. Lupus. 1998; 7 Suppl 2:5132), thrombosis (Tincani A. et al., Lupus 1998; 7 Suppl 2:S107-9), granulomatosis, Wegener's granulomatosis, arteritis, Takayasu's arteritis and Kawasaki syndrome (Praprotnik S. et al., Wien Klin Wochenschr 2000 Aug. 25; 112 (15-16):660); anti-factor VIII autoimmune disease (Lacroix-Desmazes S. et al., Semin Thromb Hemost. 2000; 26 (2):157); vasculitises, necrotizing small vessel vasculitises, microscopic polyangiitis, Churg and Strauss syndrome, glomerulonephritis, pauci-immune focal necrotizing glomerulonephritis, crescentic glomerulonephritis (Noel L H. Ann Med Interne (Paris). 2000 May; 151 (3):178); antiphospholipid syndrome (Flamholz R. et al., J Clin Apheresis 1999; 14 (4):171); heart failure, agonist-like beta-adrenoceptor antibodies in heart failure (Wallukat G. et al., Am J Cardiol. 1999 Jun. 17; 83 (12A):75H), thrombocytopenic purpura (Moccia F. Ann Ital Med Int. 1999 April-June; 14 (2):114); hemolytic anemia, autoimmune hemolytic anemia (Efremov D G. et al., Leuk Lymphoma 1998 January; 28 (3-4):285), gastrointestinal diseases, autoimmune diseases of the gastrointestinal tract, intestinal diseases, chronic inflammatory intestinal disease (Garcia Herola A. et al., Gastroenterol Hepatol. 2000 January; 23 (1):16), celiac disease (Landau Y E. and Shoenfeld Y. Harefuah 2000 Jan. 16; 138 (2):122), autoimmune diseases of the musculature, myositis, autoimmune myositis, Sjogren's syndrome (Feist E. et al., Int Arch Allergy Immunol 2000 September; 123 (1):92); smooth muscle autoimmune disease (Zauli D. et al., Biomed Pharmacother 1999 June; 53 (5-6):234), hepatic diseases, hepatic autoimmune diseases, autoimmune hepatitis (Manns M P. J Hepatol 2000 August; 33 (2):326) and primary biliary cirrhosis (Strassburg C P. et al., Eur J Gastroenterol Hepatol. 1999 June; 11 (6):595).

Examples of organ/tissue specific autoimmune diseases comprise cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases comprise atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), Wegener's granulomatosis, Takayasu's arteritis, Kawasaki syndrome (Praprotnik S. et al., Wien Klin Wochenschr 2000 Aug. 25; 112 (15-16):660), anti-factor VIII autoimmune disease (Lacroix-Desmazes S. et al., Semin Thromb Hemost. 2000; 26 (2):157), necrotizing small vessel vasculitis, microscopic polyangiitis, Churg and Strauss syndrome, pauci-immune focal necrotizing and crescentic glomerulonephritis (Noel L H. Ann Med Interne (Paris). 2000 May; 151 (3):178), antiphospholipid syndrome (Flamholz R. et al., J Clin Apheresis 1999; 14 (4):171), antibody-induced heart failure (Wallukat G. et al., Am J Cardiol. 1999 Jun. 17; 83 (12A):75H), thrombocytopenic purpura (Moccia F. Ann Ital Med Int. 1999 April-June; 14 (2):114; Semple J W. et al., Blood 1996 May 15; 87 (10):4245), autoimmune hemolytic anemia (Efremov D G. et al., Leuk Lymphoma 1998 January; 28 (3-4):285; Sallah S. et al., Ann Hematol 1997 March; 74 (3):139), cardiac autoimmunity in Chagas' disease (Cunha-Neto E. et al., J Clin Invest 1996 Oct. 15; 98 (8):1709) and anti-helper T lymphocyte autoimmunity (Caporossi A P. et al., Viral Immunol 1998; 11 (1):9).

Examples of autoimmune rheumatoid diseases comprise rheumatoid arthritis (Krenn V. et al., Histol Histopathol 2000 July; 15 (3):791; Tisch R, McDevitt H O. Proc Natl Acad Sci units S A 1994 Jan. 18; 91 (2):437) and ankylosing spondylitis (Jan Voswinkel et al., Arthritis Res 2001; 3 (3): 189).

Examples of autoimmune glandular diseases comprise pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome. diseases comprise autoimmune diseases of the pancreas, Type 1 diabetes (Castano L. and Eisenbarth G S. Ann. Rev. Immunol. 8:647; Zimmet P. Diabetes Res Clin Pract 1996 October; 34 Suppl:S125), autoimmune thyroid diseases, Graves' disease (Orgiazzi J. Endocrinol Metab Clin North Am 2000 June; 29 (2):339; Sakata S. et al., Mol Cell Endocrinol 1993 March; 92 (1):77), spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), idiopathic myxedema (Mitsuma T. Nippon Rinsho. 1999 August; 57 (8):1759), ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), autoimmune prostatitis (Alexander R B. et al., Urology 1997 December; 50 (6):893) and Type I autoimmune polyglandular syndrome (Hara T. et al., Blood. 1991 Mar. 1; 77 (5):1127).

Examples of autoimmune gastrointestinal diseases comprise chronic inflammatory intestinal diseases (Garcia Herola A. et al., Gastroenterol Hepatol. 2000 January; 23 (1):16), celiac disease (Landau Y E. and Shoenfeld Y. Harefuah 2000 Jan. 16; 138 (2):122), colitis, ileitis and Crohn's disease.

Examples of autoimmune cutaneous diseases comprise autoimmune bullous skin diseases, such as, but not limited to, pemphigus vulgaris, bullous pemphigoid and pemphigus foliaceus, discoid lupus erythematosus.

Examples of autoimmune hepatic diseases comprise hepatitis, autoimmune chronic active hepatitis (Franco A. et al., Clin Immunol Immunopathol 1990 March; 54 (3):382), primary biliary cirrhosis (Jones D E. Clin Sci (Colch) 1996 November; 91 (5):551; Strassburg C P. et al., Eur J Gastroenterol Hepatol. 1999 June; 11 (6):595) and autoimmune hepatitis (Manns M P. J Hepatol 2000 August; 33 (2):326).

Examples of autoimmune neurological diseases comprise multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83; Oshima M. et al., Eur J Immunol 1990 December; 20 (12):2563), neuropathies, motor neuropathies (Kornberg A J. J Clin Neurosci. 2000 May; 7 (3):191); Guillain-Barre syndrome and autoimmune neuropathies (Kusunoki S. Am J Med Sci. 2000 April; 319 (4):234), myasthenia, Lambert-Eaton myasthenic syndrome (Takamori M. Am J Med Sci. 2000 April; 319 (4):204); paraneoplastic neurological diseases, cerebellar atrophy, paraneoplastic cerebellar atrophy and stiff-man syndrome (Hiemstra H S. et al., Proc Natl Acad Sci units S A 2001 Mar. 27; 98 (7):3988); non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies (Antoine J C. and Honnorat J. Rev Neurol (Paris) 2000 January; 156 (1):23); dysimmune neuropathies (Nobile-Orazio E. et al., Electroencephalogr Clin Neurophysiol Suppl 1999; 50:419); acquired neuromyotonia, arthrogryposis multiplex congenita (Vincent A. et al., Ann N Y Acad Sci.

1998 May 13; 841:482), neuritis, optic neuritis (Soderstrom M. et al., J Neurol Neurosurg Psychiatry 1994 May; 57 (5):544) and neurodegenerative diseases.

Examples of autoimmune muscular diseases comprise myositis, autoimmune myositis and primary Sjogren's syndrome (Feist E. et al., Int Arch Allergy Immunol 2000 September; 123 (1):92) and smooth muscle autoimmune disease (Zauli D. et al., Biomed Pharmacother 1999 June; 53 (5-6):234).

Examples of autoimmune nephric diseases comprise nephritis and autoimmune interstitial nephritis (Kelly C J. J Am Soc Nephrol 1990 August; 1 (2):140).

Examples of autoimmune diseases related to reproduction comprise repeated fetal loss (Tincani A. et al., Lupus 1998; 7 Suppl 2:S107-9).

Examples of autoimmune connective tissue diseases comprise ear diseases, autoimmune ear diseases (Yoo T J. et al., Cell Immunol 1994 August; 157 (1):249) and autoimmune diseases of the inner ear (Gloddek B. et al., Ann N Y Acad Sci 1997 Dec. 29; 830:266).

Examples of systemic autoimmune diseases comprise systemic lupus erythematosus (Erikson J. et al., Immunol Res 1998; 17 (1-2):49) and systemic sclerosis (Renaudineau Y. et al., Clin Diagn Lab Immunol. 1999 March; 6 (2):156); Chan O T. et al., Immunol Rev 1999 June; 169:107).

Examples of transplantation-related diseases include, but are not limited to, graft rejection, chronic graft rejection, subacute graft rejection, hyperacute graft rejection, acute graft rejection and graft-versus-host disease (GVHD).

Examples of inflammatory/inflammation-associated diseases include, but are not limited to, restenosis following percutaneous transluminal coronary angioplasty (PTCA), restenosis following PTCA with stent implantation, myocardial infarction, inflammation associated with mechanical injury, neurodegenerative diseases, ulcers, prosthetic implants, menstruation, septic shock, anaphylactic shock, toxic shock syndrome, cachexia, gangrene, musculo-skeletal inflammation, idiopathic inflammation.

Therefore, the devices and methods of the present invention can be used to treat a broad range of diseases associated with pathological immune responses, such as autoimmune diseases, transplantation-related diseases and inflammatory/inflammation-related diseases, with improved safety and effectiveness relative to prior art methods which involve administration of harmful immunosuppressive drugs, and/or which inherently and unknowingly involve counterproductive and harmful administration of pro-inflammatory mediators, as is presently taught for the first time in the art.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

Example 1

Treatment of an Autoimmune Disease (SLE) by Administration of Syngeneic Apoptotic Lymphocytes Introduction: Autoimmune diseases, such as systemic lupus erythematosus (SLE), include numerous highly debilitating and/or lethal diseases for which there is no satisfactory or optimal therapy. An optimal strategy for treating such diseases would be to present targeted antigens to the immune system of an individual afflicted with such a disease in such a way as to induce tolerance to such antigens by the immune system of the individual. An optimal way to achieve this goal would be to employ autologous apoptotic cells, which would obviate or minimize the necessity for administration of toxic immunosuppressive agents, the standard means of treatment in the art. While various approaches have been proposed in the prior art for using autologous cells to induce such therapeutic immune tolerance, such approaches suffer from various drawbacks, including suboptimal effectiveness, and/or failure to demonstrate effectiveness in humans. While reducing the present invention to practice, a method of effectively inducing immune tolerance so as to enable treatment of a systemic autoimmune disease was unexpectedly uncovered, thereby overcoming the limitations of the prior art, as described below.

Materials and Methods:

Apoptosis induction: MRL/MpJ-Fas$^{lpr}$ and C3H-SnJ mice were obtained from Jackson Laboratories, Bar Harbor, Me. Thymocytes and splenocytes were prepared from 4 to 8 week-old mice according to standard methodology. Apoptosis of thymocytes or splenocytes was induced by either serum deprivation, 1 micromolar dexamethasone, or gamma-irradiation (66 rad). Apoptosis was confirmed via flow cytometric analysis of annexin-FITC staining, DNA fragmentation and propidium iodide staining of fragmented DNA.

Treatment protocol: MRL/MpJ-Fas$^{lpr}$ and C3H-SnJ mice obtained from Jackson Laboratories, Bar Harbor, Me., were administered a total of $5\times10^6$ syngeneic sex- and age-matched apoptotic cells per mouse, as 5 weekly injections of $1\times10^6$ cells per mouse. The route of administration was intravenous injection into the tail vein of cells suspended in a volume of 200 microliters. As negative controls, syngeneic, sex- and age-matched mice were injected with vehicle (saline) only.

Autoimmune response—anti-self DNA antibody ELISA: Serum samples were obtained immediately prior to treatment and at two-week intervals following treatment. The immune response was evaluated by quantifying serum antibodies specific for single-stranded DNA (ssDNA) and double-stranded DNA (dsDNA) by enzyme-linked immunosorbent assay (ELISA) of 100-fold diluted serum.

Pathological evaluation: Mice were examined every day for pathological signs of disease and once a month for hematuria or proteinurea. After four months the mice were sacrificed and their were kidneys examined histologically and via immunofluorescence.

Experimental Results:

In the study presented herein, one of the classical animal models of SLE-like disease, the MRL/MpJ-Fas$^{lpr}$ mouse model, was used to analyze the effects of administration of syngeneic apoptotic lymphocytes on disease pathogenesis. MRL/MpJ-Fas$^{lpr}$ mice develop SLE-like disease due to mutation in Fas, a receptor that mediates apoptosis and activation of induced cell death of the immune system. Since in SLE patients, as well as in MRL/MpJ-Fas$^{lpr}$ mice, the development of autoantibodies and kidney disease are the most specific pathophysiological parameters, those parameters were evaluated in MRL/MpJ-Fas$^{lpr}$ mice following administration of apoptotic cells.

Two groups of age- and sex-matched MRL/MpJ-Fas$^{lpr}$ mice were compared. In the experimental group, $1\times10^6$ syngeneic apoptotic cells were injected intravenously into each of five mice, five times at weekly intervals, for a total dose of $5\times10^6$ cells per mouse. In the negative control group, 200 microliters of saline carrier alone was injected. IgG anti-ssDNA levels were then measured via ELISA at two-week intervals and were found to be comparable in both groups prior to treatment, with a mean O.D. value of 0.096 plus/minus 0.018 (FIG. 1). When the antibody levels were compared 10 weeks after the start of treatments, mice administered with vehicle alone displayed, as expected in mice which develop lupus-like disease, increased anti-ssDNA antibody levels, as evidenced by an ELISA O.D. value of 0.308 plus/minus 0.029 (p<0.0000, student t-test). However, mice injected with $1\times10^6$ syngeneic apoptotic cells unexpectedly had significantly reduced levels of autoantibodies, with an ELISA O.D. value obtained of 0.193 plus/minus 0.017 (p<0.0000, student t-test).

In order to control for baseline changes in whole IgM titers, serum samples from the control and experimental groups were evaluated at 2-week intervals for IgM. The ELISA O.D. values obtained at these intervals for negative control mice injected with saline were 0.198 plus/minus 0.017, 0.205 plus/minus 0.02, 0.300 plus/minus 0.033 and 0.378 plus/minus 0.037; and for mice treated with apoptotic cells were 0.108(+0.03), 0.170(+0.07), 0.186(+0.04) and 0.203(+0.8). Statistical analysis indicated that was no significant difference between the two groups. In contrast, anti-ssDNA IgG levels were unexpectedly found to significantly decrease following injection of apoptotic cells, with ELISA O.D. values of 0.132 plus/minus 0.09, 0.196 plus/minus 0.019, 0.244 plus/minus 0.022, and 0.308 plus/minus 0.029 being obtained for control mice injected with saline, as opposed to 0.109 plus/minus 0.012 (p=non-significant), 0.129 plus/minus 0.15, p<0.04), 0.166 plus/minus 0.014, (p<0.04), 0.192 plus/minus 0.17) (p<0.01), for mice injected with syngeneic apoptotic thymocytes. As shown in FIG. 1, at 16 weeks of age, i.e. 10 weeks post-treatment, a surprising marked decrease in anti-ssDNA antibody titers was noted in all mice injected with the apoptotic cells.

Figure 2:
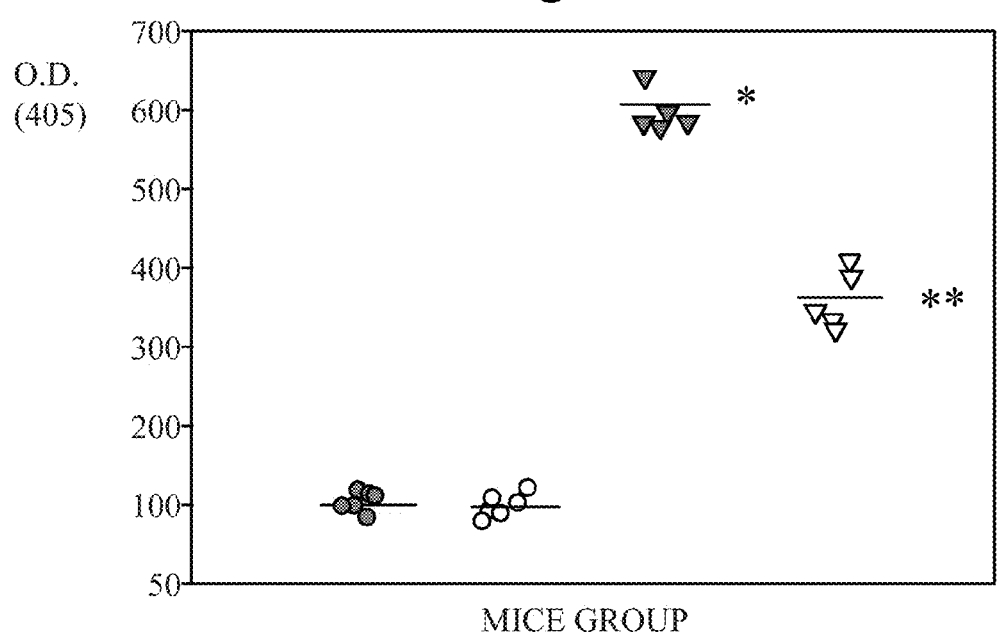
FIG. 2 is a histogram depicting reduction of serum anti-double-stranded DNA antibodies in MRL/MpJ-Fas$^{lpr}$ mice following treatment with syngeneic apoptotic cells. Filled circles, control group of 6 week-old MRL/lpr/lpr mice immunized with vehicle only; open circles, experimental group of 6 week-old MRL/lpr/lpr mice immunized with syngeneic apoptotic cells; filled triangles, control group after 10 weeks of treatment; open triangles, experimental group after 10 weeks of treatment.

In order to determine whether titers of anti-dsDNA autoantibodies, which are more specific to SLE than anti-ssDNA antibodies, specifically decreased as a result of apoptotic cell injection, anti-dsDNA antibody titers were measured immediately prior to treatment, and 6-8 weeks post-treatment, when the mice were sacrificed. As shown in FIG. 2, anti-dsDNA antibody titers were surprisingly found to be significantly reduced (p<0.00) in mice injected with apoptotic cells. An average O.D. value of 0.599 plus/minus 0.026 was obtained in an anti-dsDNA antibody ELISA of serum from mice injected with saline, and an average O.D. value of 0.358 plus/minus 0.038 was obtained in mice injected with the apoptotic cells.

To determine whether the disease pathology progressed in accordance with the serological data, kidney-disease was monitored in the treated and control mouse groups. None of the mice in either group displayed proteinuria or hematuria, as measured by urine-stick at 6 weeks of age, immediately prior to immunization. At 10 weeks after the start of the treatments, mice injected with saline displayed significant elevations in proteinuria and hematuria and concomitant glomerular disease, as shown in Table 1. However, as also shown in Table 1, mice injected with the apoptotic cells overall unexpectedly displayed significantly decreased proteinuria and hematuria and concomitant glomerular disease, consistent with the serological response. Strikingly, in two out of five mice treated with apoptotic cells, no deterioration or very slight deterioration was noticed.

In order to determine whether renal pathogenesis progressed in accordance with the above urinary indicators, immunofluorescent histological analyses were performed on paraffin sections of kidneys from the treated mice. Table 2 summarizes the histopathological findings in three blindly selected kidney sections of each treatment group, and surprisingly shows that mice injected with apoptotic cells displayed decreased pathogenesis in the glomeruli, vessels and tubuli.

TABLE 1

Significant decrease in proteinuria and hematuria in MRL/MpJ-Fas$^{lpr}$ mice treated with apoptotic cells.

| Mouse strain | Treatment | Proteinuria 6 weeks | Proteinuria 16 weeks | Hematuria 6 weeks | Hematuria 16 weeks |
| --- | --- | --- | --- | --- | --- |
| C3H/SnJ | None | + | + | - | - |
| MRL/MpJ-Fas$^{lpr}$ | saline only | + | ++ | - | ++ |
| | | + | +++ | - | + |
| | | + | ++ | - | +++ |
| | | + | ++ | - | ++ |
| | | + | +++ | - | + |
| | apoptotic cells | + | ++ | - | + |
| | | + | + | - | + |
| | | + | + | - | + |
| | | + | + | - | - |
| | | + | ++ | - | + |

C3H/SnJ, normal mice.
"+", normal proteinuria. "-", normal hematuria.
Pathological index is proportional to the number of plus signs.

TABLE 2

Histological and indirect immunofluorescence evaluation for IgG deposits in MRL/MpJ-Fas$^{lpr}$

| Mouse strain | Treatment | Histology Glomeruli | Histology Vessels | Histology Tubuli | Indirect immunofluorescence Glomeruli | Indirect immunofluorescence Tubuli |
| --- | --- | --- | --- | --- | --- | --- |
| C3H/SnJ | None | - | - | - | - | - |
| MRL/MpJ-Fas$^{lpr}$ | Saline only | ++ | +++ | + | +++ | +++ |
| | | ++ | ++ | +/++ | ++++ | +++ |
| | | ++ | ++/+++ | -/+ | +++ | ++ |
| | Apoptotic cells | + | ++ | - | + | + |
| | | ++ | + | - | ++ | + |
| | | + | + | + | +++ | + |

C3H/SnJ, normal mice.
Pathological index is proportional to the number of plus signs.
"-", healthy tissue.

Conclusion: The above-described results unexpectedly demonstrate that administration of dying cells, such as syngeneic apoptotic lymphocytes, to a mammal having a lymphocyte-mediated disease, particularly an autoimmune disease, and most particularly SLE, can be used to effectively inhibit pathogenesis of the disease, and hence to effectively treat such a disease in a human, thereby overcoming the limitations of the prior art which fails to provide adequate solutions for treatment of such diseases.

Example 2

Monocytes Suspended Ex-Vivo Undergo Necrosis and Produce Whereas Substrate-Adherent Ex-Vivo Monocytes Undergo Apoptosis without Pro-Inflammatory Mediator Production: Method of Improving Prior Art Apheresis Procedures Introduction: Immune/hematological diseases, such as graft-versus-host disease (GVHD), include a large number of diseases which are associated with significant mortality and morbidity, and for which no satisfactory/optimal treatments are available. In a very large number of cases the optimal strategy for treating such diseases involves performing apheresis procedures. Typically, apheresis procedures involve removing blood from an individual, separating the blood into fractions and performing therapeutic treatment of specific fractions, removing undesirable pathological fractions and reinfusing the remainder to the individual, or harvesting desired may be associated with undesirable side-effects and/or suboptimal effectiveness. Therefore, a potentially optimal strategy for performing apheresis involves identifying harmful effects of apheresis procedures on blood components so as to enable design of optimal methods and devices for performing apheresis. While reducing the present invention to practice, as described below, the induction of necrosis of monocytes, and the concomitant secretion of harmful pro-inflammatory mediators thereby resulting from their ex-vivo suspension, as typically occurs during apheresis procedures was unexpectedly uncovered, as opposed to serum deprivation and substrate-adherent conditions which were surprisingly found to induce apoptosis of monocytes, in the absence of the aforementioned secretion of pro-inflammatory mediators. As such, the experimental results described below overcome the limitations of the prior art by teaching for the first time that apheresis procedures involving subjecting monocytes to serum deprivation/substrate adherent conditions can prevent the harmful pro-inflammatory effects inherent to prior art apheresis procedures.

Materials and Methods:

Cell isolation and culture: Human mononuclear cells were isolated from heparinized peripheral blood by density gradient centrifugation. The isolated mononuclear cells were separated into monocyte, B-cell and T-cell populations by positively selecting monocytes as the CD14+ fraction by magnetic bead separation (Miltenyi Biotec., Auburn, Calif., USA), positively selecting B-cells as the CD22+ fraction, and negatively selecting T-cells as the CD14-CD22- fraction. Purity was greater than 95 percent for monocytes, greater than 95 percent for B-cells and greater than 88 percent for T-cells. Polymorphonuclear cells (neutrophils) were separated by density gradient centrifugation of the upper fraction obtained following incubation of peripheral blood with Plasmasteril (GmbH, Bad Homburg, Germany). When necessary, red blood cells in the pellets were hemolysed under hypoosmotic conditions. Anti-CD15 magnetic beads were employed to purify neutrophils to greater than 95 percent purity. Alternately, monocyte isolation was performed concomitantly with apoptosis induction by adherence, as described below.

Cell death induction: Leukocyte death was induced by serum deprivation or suspension, and necrosis of leukocytes was fas-induced. For serum deprivation treatment, monocytes were incubated at 37 degrees centigrade in serum-free RPMI culture medium in polypropylene tubes. Necrosis was induced hyperthermally by incubation at 56 degrees centigrade for 20 minutes, and confirmed by greater than 95 percent trypan blue positive cells and swollen cells detected via flow cytometry forward-scatter.

Monocyte apoptosis was induced via substrate-adherence+serum withdrawal by either of two methods. In the first method, monocytes isolated using anti-CD14 conjugated magnetic beads (Miltenyi Biotech, Bergisch Gladbach, Germany) were incubated in serum-free RPMI at a concentration of 7.5 million to 20 million cells per milliliter in 35 mm diameter tissue culture-treated Petri dishes (Corning, USA, Cat. No. 430165). In the second method, isolated PBMCs were incubated in serum-free RPMI at a concentration of 15 million to 30 million cells per milliliter in 35 mm diameter tissue culture-treated Petri dishes (Corning, USA, Cat. No. 430165), and after 40 minutes, non-adherent cells were washed away, leaving behind the adherent, apoptotic monocytes.

Cell death assays: Apoptosis and necrosis were detected by double staining with annexin-V-FITC (Roche Diagnostics GmbH, Mannheim, Germany) and propidium iodide, and were verified by propidium iodide staining as well as by measuring the hypodiploid portion of the cell cycle histogram, as previously described [20].

Cell death inhibition assays: In some of the experiments the cells were pretreated or co-treated (as indicated) with different reagents to achieve cell death inhibition. For apoptosis inhibition anti-Fas inhibitory mAb ZB4 (MBL, Nagoya, Japan) was used at a concentration of 1 microgram/ml, and anti-Fas mAb DM542A (Acris Antibodies, Hiddenhausen, Germany) was used. Caspase-1 was inhibited using caspase-1 (ICE) fmk inhibitor Z-WEHD (R & D Systems). For proteasome inhibition, cells were exposed for 45 minutes to 50 micromolar of the proteasome inhibitor MG132 (Calbiochem, San Diego, Calif., USA). P38 and JNK were inhibited using 10 micromolar SB203580 (Calbiochem, Darmstadt, Germany) or 20 millimolar L-JNKI1 (Alexis, San Diego, Calif., USA), respectively. For transcription inhibition, 5 micrograms/ml Actinomycin D was used and for translation inhibition, 15 micrograms/ml cycloheximide (Sigma, St. Louis, Mo., USA) was used. Monocyte activation was induced with 500 micrograms/ml, 1 mg/ml Zymosan, or 1 microgram/ml of LPS (Sigma, St. Louis, Mo., USA).

Gene Expression Analysis: Total RNA was isolated by using the EZ-RNA isolation kit (Biological Industries Co., Kibbutz Bet-Haemek, Israel). Quantity was determined by means of spectrophotometry and quality by gel electrophoresis. GEArray gene expression array systems hGEA9912090, hGEA9913030 and hGEA9913040 (SuperArray, Bethesda, Md., USA) were used. Each array consists of 56 coordinates containing specific cDNA fragments spotted in duplicates as well as control sequences [PUC18 as negative control; beta-actin and glyceraldehyde-3-phosphate dehydrogenase (GAPDH) as positive control]. cDNA probes were synthesized from total RNA samples using the manufacturer's primer mix as a reverse transcriptase primer. The cDNA probes were hybridized to gene-specific cDNA fragments spotted on the membranes. The relative expression level of the genes was adjusted based on intensity of hybridization signals to the housekeeping genes beta-actin and GAPDH, then gene expression was quantified by scanning densitometry. Each experiment was performed at least three times to ensure reproducibility of results.

Cytokine/chemokine analysis: concentrations of the cytokines/chemokines IL-4, IL-6, IL-8, IFN-gamma, TNF-alpha, TGF-beta, and MIP-1-alpha, were determined via ELISA immunoassay (R&D systems, Minneapolis, Minn., USA) according to the instructions provided by the manufacturer.

Western immunoblotting: Polyclonal antibodies to p38, phospho-p38 (Thr$^{180}$/Tyr$^{182}$), JNK, and phospho-JNK (Thr$^{183}$/Tyr$^{185}$) were purchased from Cell Signaling (Beverly, Mass., USA), and to IkappaB-alpha from Santa Cruz Biotechnology, Inc. (Santa Cruz Calif., USA). Cells were lysed and 30 micrograms of protein was separated via 10 percent SDS-PAGE, and the separated proteins were blotted onto a transfer membrane, the blotted membrane was blocked in 20 percent low-fat milk in PBST solution (PBS containing 0.05-0.1 percent Tween-20) for IkappaB detection, or was blocked in TBST solution (TBS solution containing 0.1 percent Tween-20) for p38 or JNK detection. The membrane was incubated with primary antibody for 2 hours at room temperature or overnight at 4 degrees centigrade, then washed with PBST or TBST and incubated for 30 minutes in a solution containing a 1:10,000 dilution of protein A-HRP (Amersham Biosciences, Buckinghamshire, England). Labeled proteins were visualized with the EZ-ECL detection kit (Beit-Haemek Industries, Kibbutz Beit-Haemek, Israel)

Figure 3:
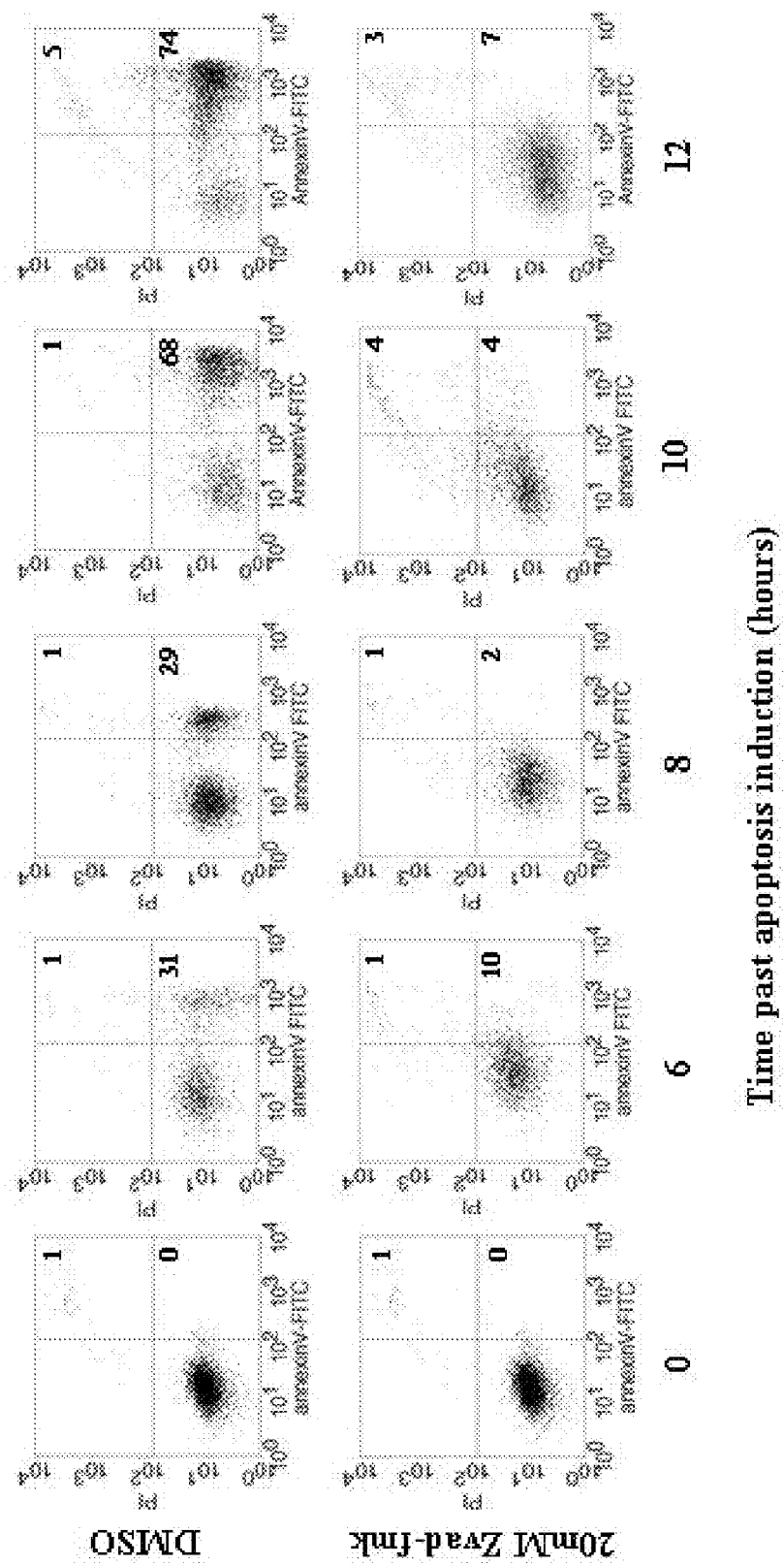
FIG. 3. is a set of fluorescence activated cell sorting (FACS) dot plots depicting induction of monocyte apoptosis by serum withdrawal and substrate-adherence. More than 70 percent of monocytes were annexin V-positive PI-negative by 12 hours indicating early apoptosis. Secondary necrotic cells represented less than 5 percent of the cells as indicated by annexin V-positive, propidium iodide (PI)-positive cells. The specificity of the apoptotic process was further shown by marked inhibition in the presence of 20 mM zVAD-fmk. The percentage of early apoptotic and secondary necrotic cells is indicated within each histogram. Data is representative of six different experiments.
Figure 4:
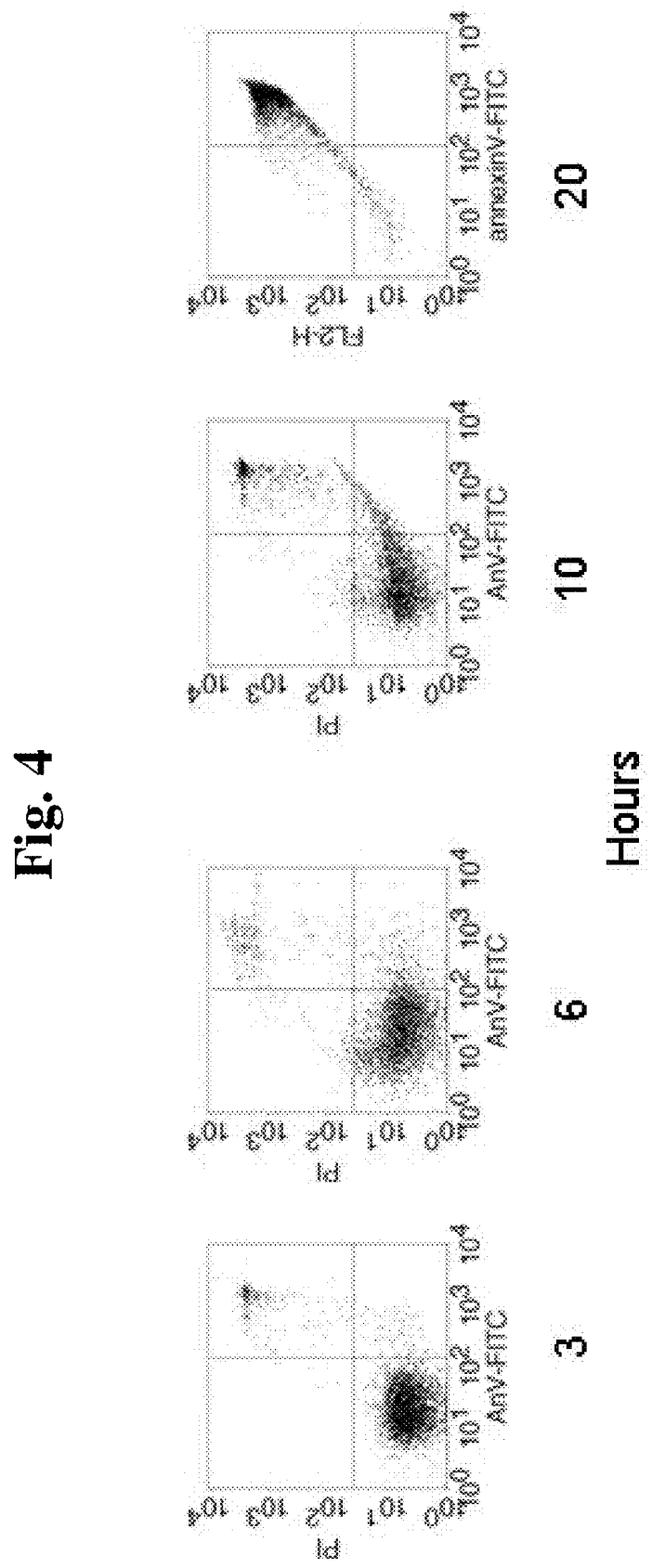
FIG. 4. is a set of fluorescence activated cell sorting (FACS) dot plots depicting that suspension+serum-withdrawal-induced death of monocytes is non-apoptotic and shows features of necrosis. Prevention of contact in addition to serum withdrawal switched the mechanism of death. Cell numbers were reduced progressively whereas the percentage of annexin+PI− remain constant and low. Cells were becoming directly annexin+PI+ and 20 mM zVAD-fmk did not reduce the rate of death (not shown).
Figure 5A:
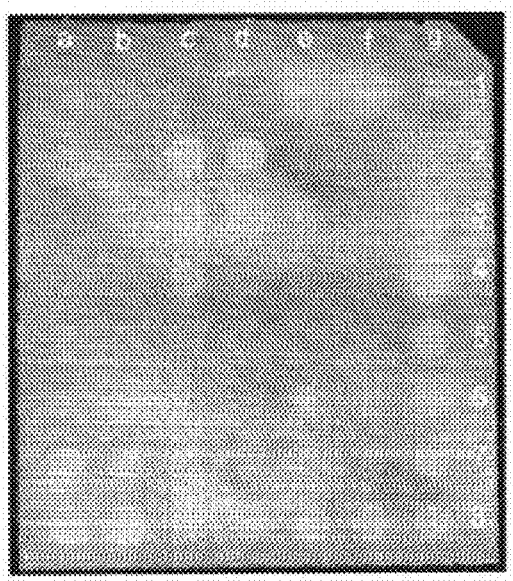
FIGS. 5a-c depict de-novo transcription of pro-inflammatory cytokine/chemokine mRNAs by monocytes subjected to suspension+serum deprivation.
Figure 5B:
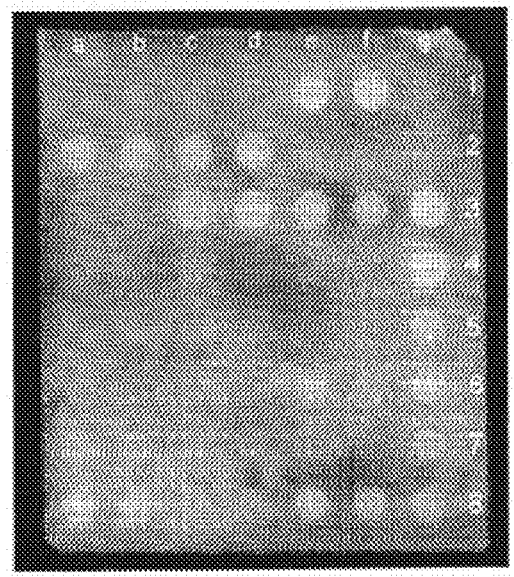
Figure 5C:
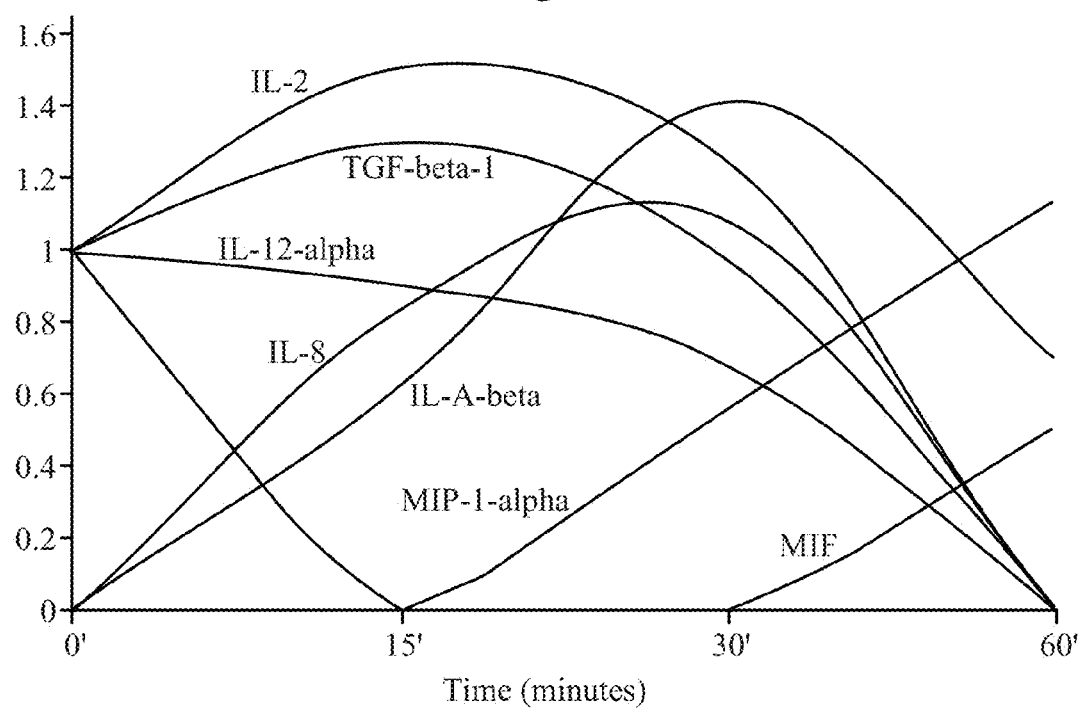
Figure 6A:
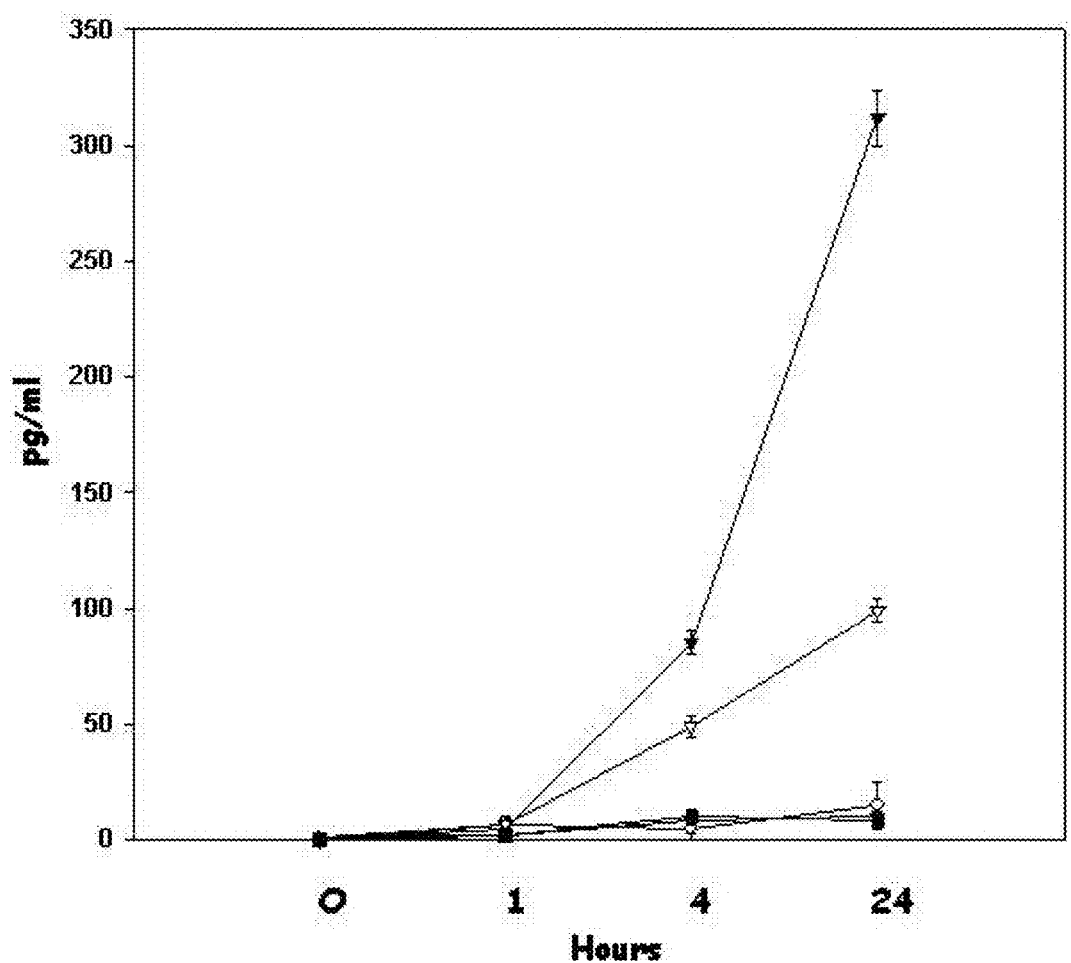
FIG. 6a. is a data plot depicting that the pro-inflammatory cytokine IL-1-beta is produced by monocytes subjected to suspension+serum withdrawal. Control PBMCs exhibit elevation of IL-1-beta secretion following suspension+serum withdrawal (open triangles). Absence of IL-1-beta secretion by magnetically isolated monocytes (closed triangles), B-lymphocytes (open circles), T-lymphocytes (closed circles), and polymorphonuclear cells (closed squares), shows that IL-1-beta secretion is specific to monocytes.
Figure 6B:
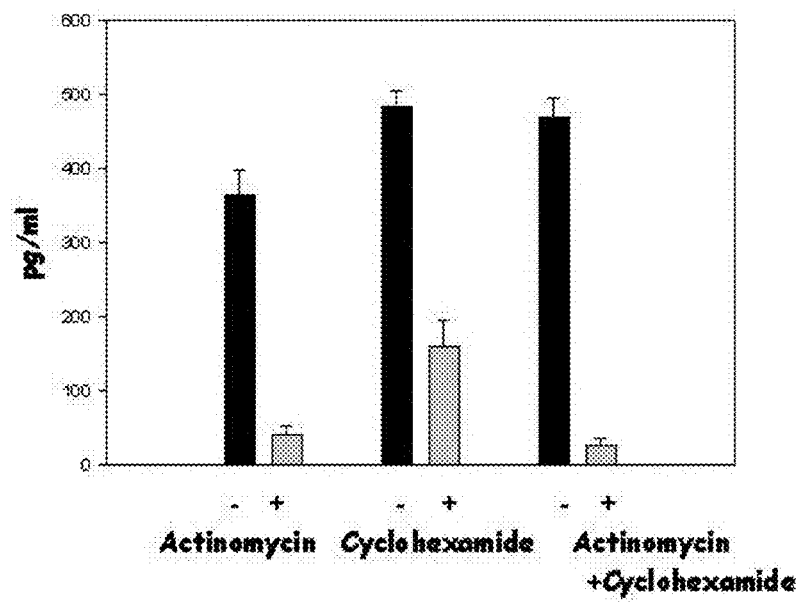
FIG. 6b is a histogram depicting that pro-inflammatory cytokine/chemokine mRNA and protein are transcribed and translated de-novo by monocytes subjected to suspension+serum withdrawal Inhibition of transcription activity with actinomycin D and translational activity with cycloheximide shows marked inhibition in cytokine secretion.
Figure 7A:
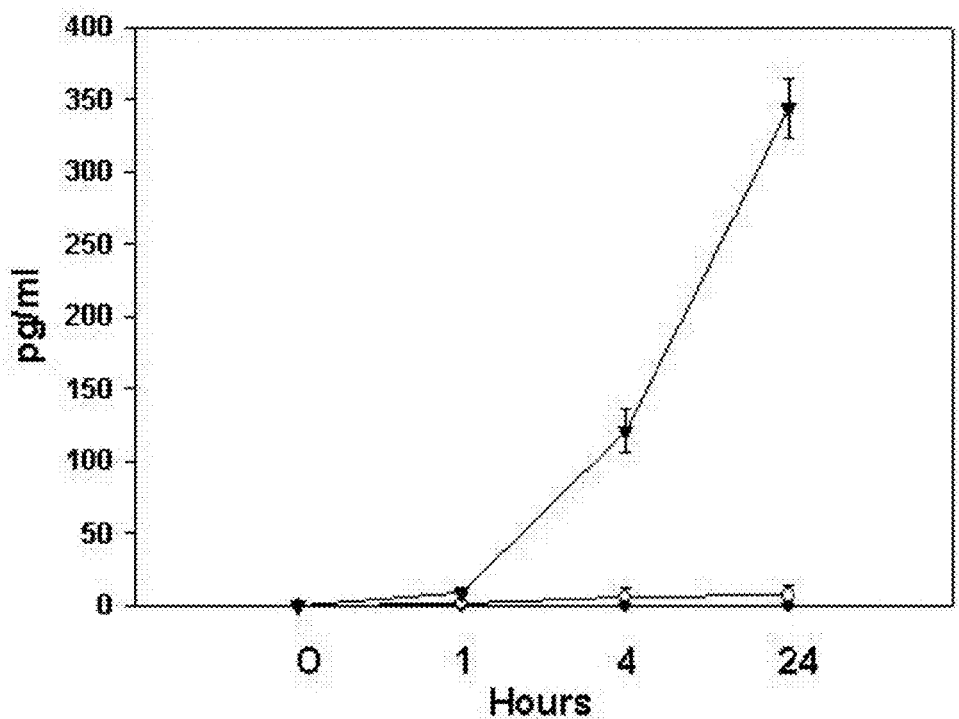
FIG. 7a is an ELISA data plot depicting that secretion of IL-1-beta is neither caspase 3- nor caspase 1-dependent and is specific to monocytes subjected to suspension+serum deprivation. IL-1-beta is secreted by monocytes subjected to suspension-induced death but not from viable monocytes, monocytes subjected to hyperthermia-induced necrosis, or apoptotic monocytes. Levels of IL-1-beta were measured by ELISA at 0, 1, 4, and 24 hours following incubation of viable monocytes (closed circles), monocytes rendered necrotic via hyperthermia (open circles), monocytes rendered apoptotic via serum deprivation (open triangles), or monocytes subjected to suspension-induced death (closed triangles).
Figure 7B:
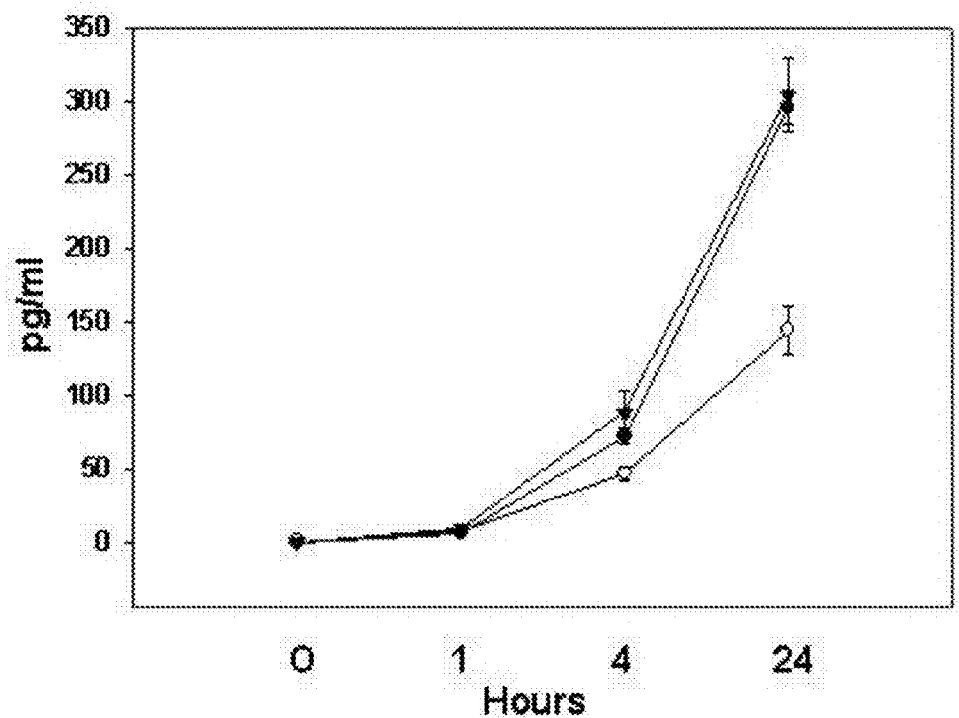
FIG. 7b is an ELISA data plot depicting secretion of IL-1-beta by monocytes subjected to suspension-induced death (closed triangles, in 20 micromolar DMSO) was neither inhibited with the caspase 1 inhibitor, Z-WEHD (20 micromolar, closed circles), nor with the pan-caspase inhibitor ZVAD-fmk (20 micromolar, open circles). In fact, ZVAD-fmk significantly increased IL-1-beta secretion ($p<0.001$).

Experimental Results:

CD14+ monocytes were isolated and subjected to either substrate-adherence+serum deprivation, or suspension+serum adherence. Surprisingly, serum deprivation resulted in apoptosis of the cells (FIG. 3) with no decline in cell numbers for the first 10 hours, whereas suspension+serum withdrawal resulted in very rapid death with 50 percent reduction in cell numbers reached in 4 hours (FIG. 4). Very few suspended monocytes did not stain positive for propidium iodide, and from the start of suspension most of the cells were found to be positive for both annexin-V and propidium iodide in constant proportion (FIG. 4), exhibited low levels of hypodiploid staining (not shown), and displayed a sharp decline in cell numbers. Furthermore, inhibition with the pancaspase inhibitor Zvad-FMK not only did not inhibit cell death but in fact increased cell death (not shown). Taken together, these results suggested that monocytes undergoing suspension-induced death undergo necrosis rather than apoptosis. In order to further characterize this mode of death, mRNA expression of a variety of cytokines and chemokines in the suspended monocytes was examined, revealing significant upregulation of transcription of the pro-inflammatory mediators IL-1-beta, IL-8, and MIP-1-alpha mRNA (FIGS. 5a-b and 5c). Tests performed to determine whether this transcriptional activity produced secreted proteins revealed production of high levels of IL-1-beta (FIG. 6a), IL-8 (320 plus/minus 64 pg/ml), and MIP-1-alpha (320 plus/minus 64 pg/ml) that were specific to monocytes but not to neutrophils undergoing suspension. No mRNA of IL-4, IL-10, IFN-gamma, and TGF-beta was detected. As controls, tests were performed for detection of IL-4, IL-10, IFN-gamma, and TGF-beta protein production (Quantikine, R&D Systems). Of these, only IL-10 was found to be secreted, at 50-100 ng/ml, following pro-inflammatory cytokine secretion, peaking at 24 hours after the start of suspension. As shown in FIG. 6b, treatment of the cells with the transcription inhibitor actinomycin D, or the translation inhibitor cycloheximide dramatically inhibited cytokine secretion. Taken together, these findings suggest that specific transcriptional, translational, and secretory pro-inflammatory activities are initiated in monocytes subjected to suspension+serum withdrawal. The specificity of this observation to monocytes undergoing suspension was further shown by the fact that only monocytes undergoing suspension-induced death, but not dying neutrophils, dying lymphocytes (FIG. 6a), apoptotic monocytes or monocytes subjected to hyperthermia-induced necrosis secrete pro-inflammatory cytokines. Comparison of IL-1-beta secretion among apoptotic monocytes, viable monocytes, and monocytes rendered necrotic via suspension, showed that secretion is specific to cells undergoing suspension-induced death (FIG. 7a). In order to further examine whether the cytokine/chemokine secretion was related to caspase-dependent mechanisms, monocytes undergoing apoptosis were exposed to the pan-caspase inhibitor Zvad/fmk. Surprisingly, suspension-induced death of monocytes was not caspase-dependent as judged by lack of inhibition by ZVAD-fmk (FIG. 7b). Furthermore, staining with annexin-V and propidium iodide showed clearly a necrotic rather than apoptotic death (FIG. 4).

The cytokine IL-1-beta is the key initiator of the innate immunity acute inflammatory response [21, 22]. Upon NFkappaB-dependent gene transcription by lipopolysaccharide (LPS), IL-1-beta is synthesized in human monocyte-lineage cells as the biologically inactive 31 kDa precursor pro-IL-1-beta. IL-1-beta is not secreted through the classical endoplasmic reticulum-Golgi pathway [23] due to a lack in the N-terminal amino acid leader sequence that would allow translation at the endoplasmic reticulum associated ribosomes and subsequent packaging into secretory vesicles. IL-1-beta is also not stored in or released from exocytotic granules [24].

In order to be released as biologically active 17 kDa IL-1-beta, pro-IL-1-beta must be further proteolytically cleaved by caspase-1, which undergoes activation from its pro-caspase zymogenic form. Activation of P2X7 receptors by extra cellular ATP following NFkappaB activation causes phosphatidylserine (PS) flip in the plasma membrane and loss of membrane asymmetry with respect to its positioning. Readily releasable phosphatidylserine-exposing microvesicles containing 17 kDa IL-1-beta are then pinched off from the cell within a few seconds [25].

Assays were performed to verify that IL-1-beta secretion does not result from monocyte activation, and follows the immediate pattern described above upon activation. It was shown that IL-1-beta secretion was not immediate, (FIG. 6a) and was dependent on de-novo mRNA synthesis (FIG. 5b). Assays were then performed to verify whether it was caspase-1-dependent, and, as shown in FIG. 7b, specific inhibition of caspase-1 did not influence IL-1-beta secretion.

Figure 8A:
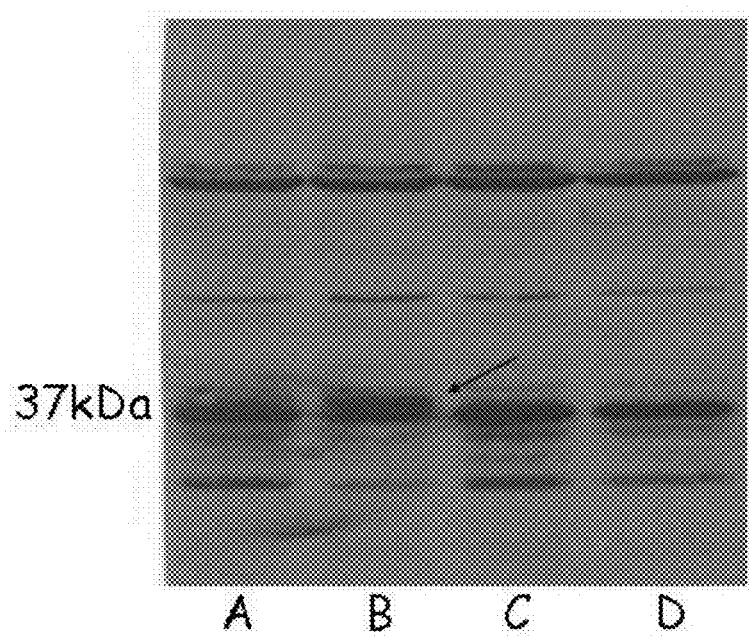
FIGS. 8a-c depict that pro-inflammatory cytokine secretion during monocyte apoptosis is not NFkappaB-dependent.
Figure 8B:
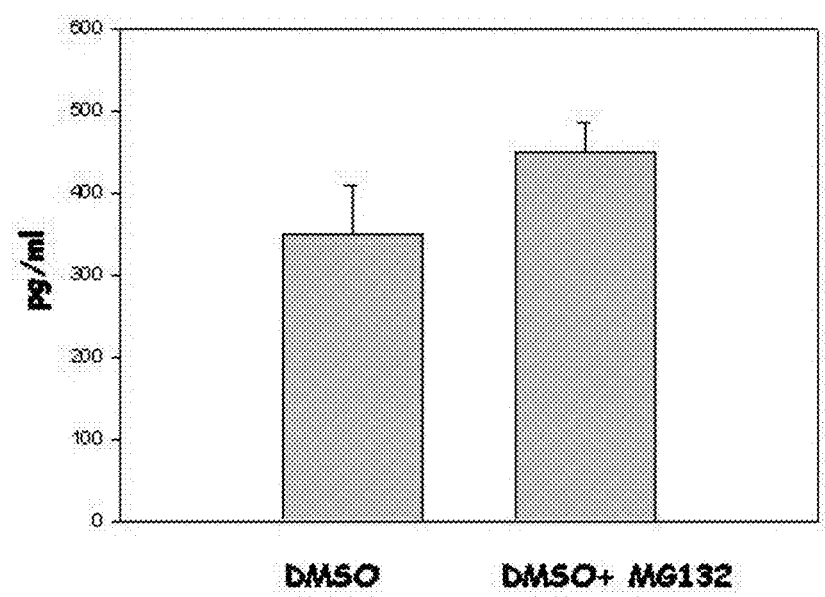
Figure 8C:
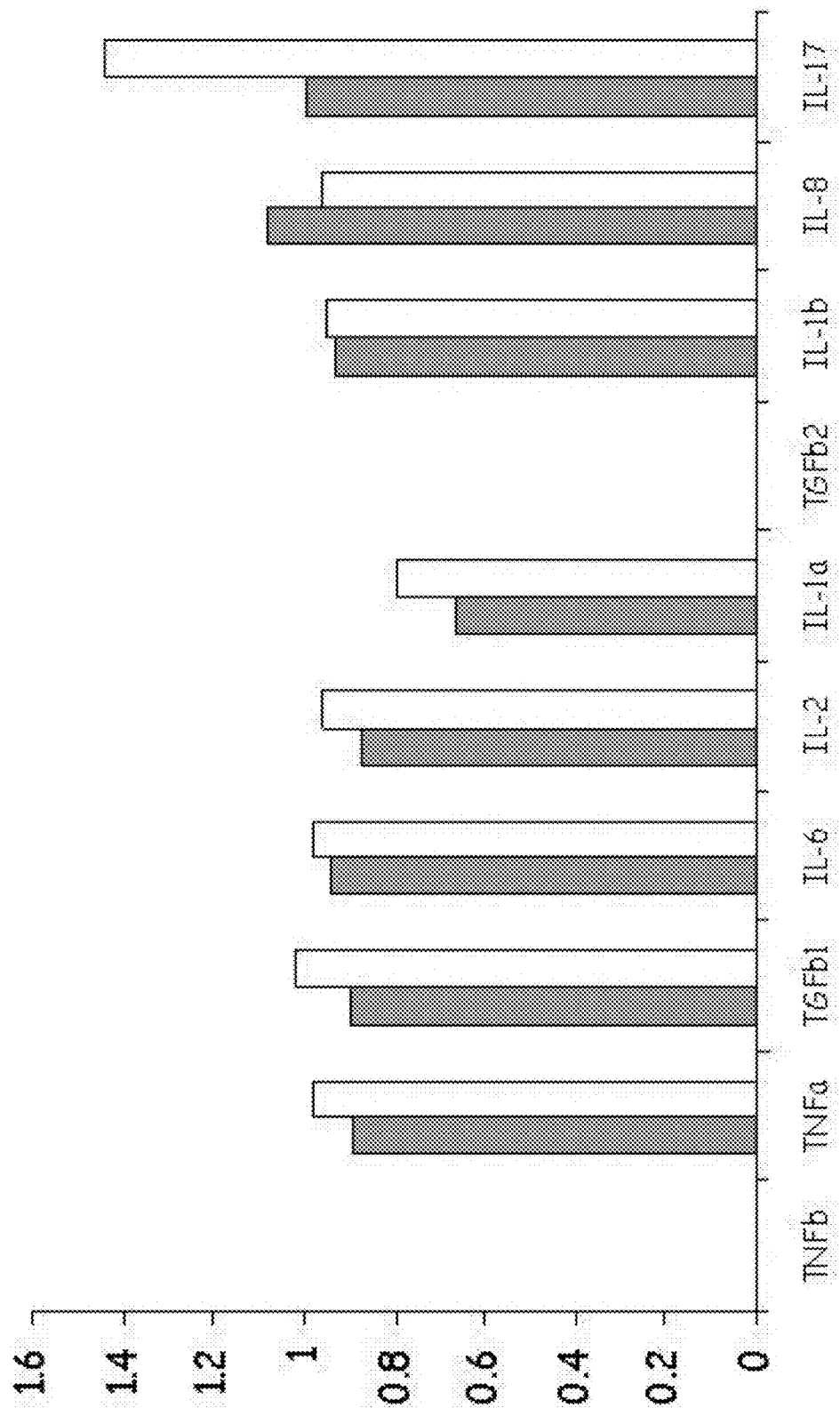

These findings strongly suggested that IL-1-beta secretion from monocytes subjected to suspension-induced death follows a different pattern than IL-1-beta secretion upon activation. Because activation is NFkappaB-dependent, and in order to verify that cytokine secretion is not a consequence of NFkappaB-dependent cell activation, a Western immunoblotting assay was performed to detect IkappaB phosphorylation and degradation. As shown in FIG. 8a, no IkappaB phosphorylation was seen. To further verify that NFkappaB was not involved, monocyte apoptosis was induced in the presence of MG132, a proteasome inhibitor that inhibits NFkappaB activation [26]. As shown in FIG. 8b, MG132 did not inhibit cytokine secretion, and even a slight increase in IL-1-beta secretion was seen, possibly due to NFkappaB inhibition of anti-apoptotic effect [27]. Furthermore, MG132 did not inhibit mRNA levels (FIG. 8c). Taken together, these results demonstrate that IL-1-beta secretion by adherent substrate-deprived dying monocytes followed a pattern distinct from that seen upon activation. IL-1-beta secretion was not immediate, was transcription- and translation-dependent, caspase-1-independent, and NFkappaB-independent.

Figure 9A:
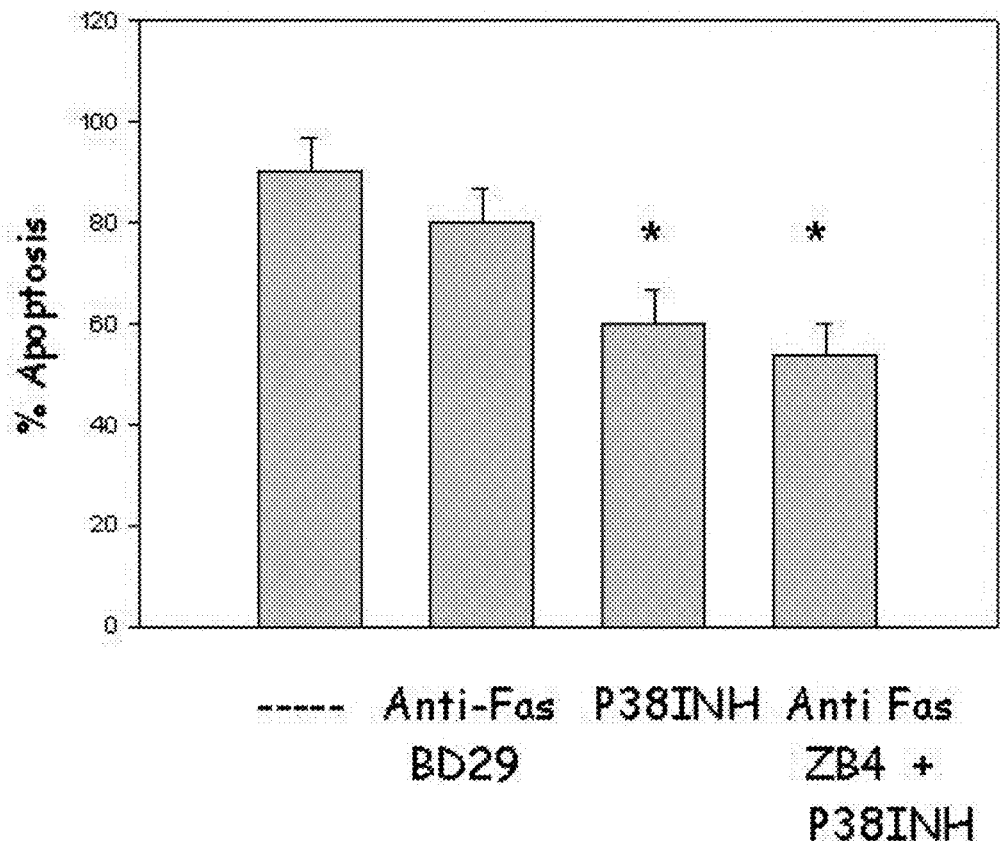
FIGS. 9a-e depict that pro-inflammatory cytokine secretion during monocyte apoptosis is p38-dependent.

Monocytes were recently shown to exhibit pro-inflammatory signaling following Fas-induced apoptosis [28]. In addition, it has been suggested that following anti-Fas mAb (CH11)-induced apoptosis, human monocytes displayed Fas-dependent IL-8 and TNF-alpha secretion, which was associated with NFkappaB activation and shown to occur even in the absence of apoptosis [29]. However, NFkappaB activation was not detected in monocytes subjected to suspension-induced death (FIGS. 8a-c). Thus, in order to exclude Fas-mediated signaling for pro-inflammatory cytokines/chemokines, monocytes undergoing apoptosis were exposed to two different Fas inhibiting antibodies. As shown in FIG. 9a, using two different inhibitory antibodies for Fas mediated apoptosis did not significantly inhibit suspension-induced monocyte death. Furthermore, both inhibitory antibodies did not decrease IL-1-beta secretion and even caused elevation in IL-1-beta levels (data not shown).

Figure 9B:
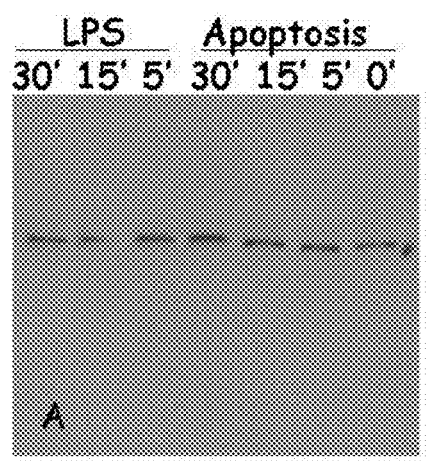
Figure 9C:
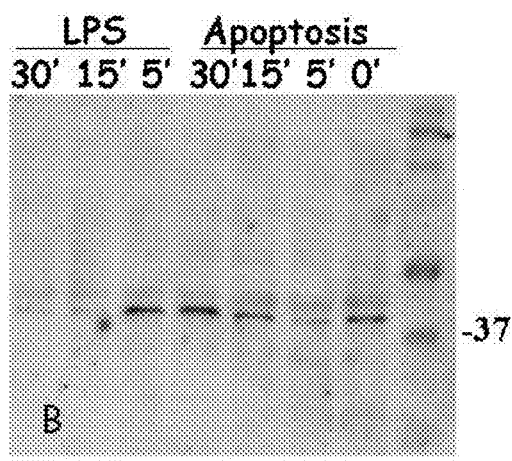
Figure 9D:
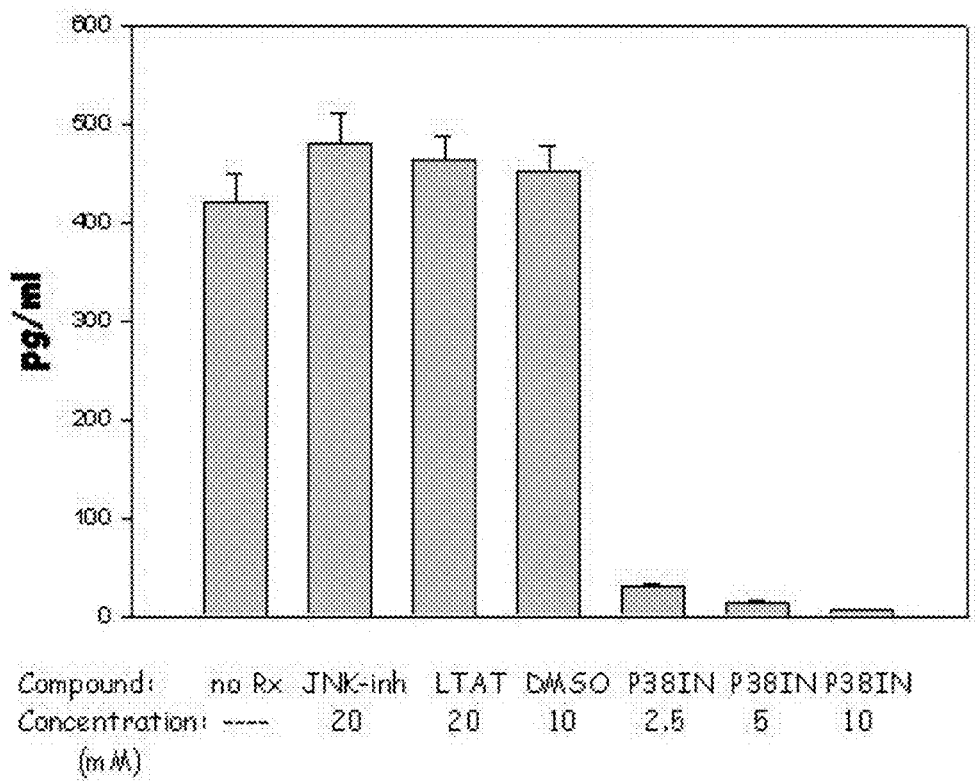
Figure 9E:
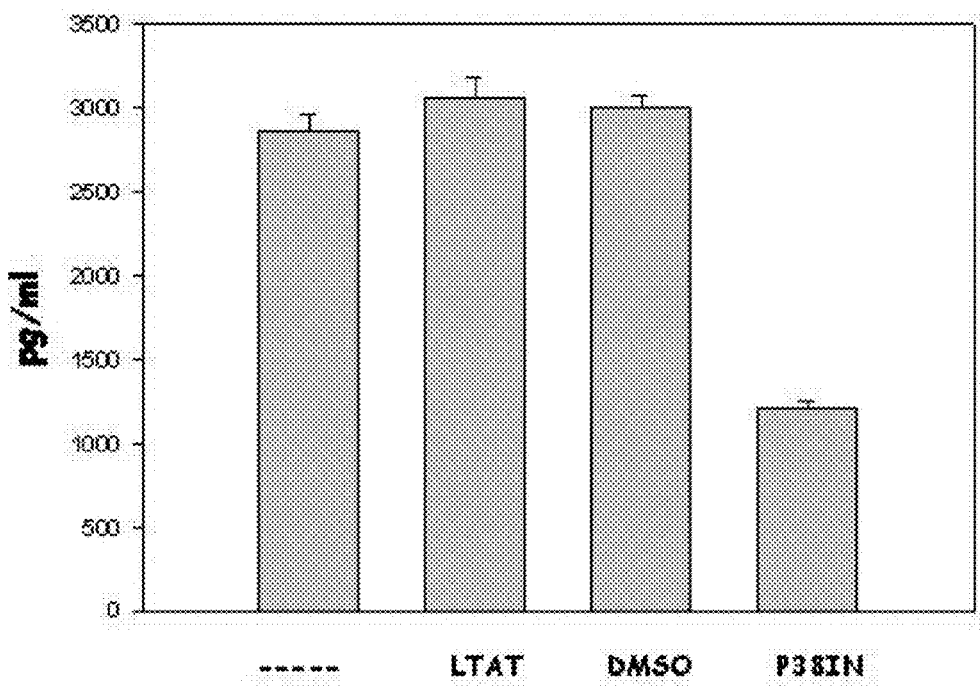

Assays were performed to verify whether MAPK kinases are involved in secretion of pro-inflammatory cytokines, since the MAPK signaling cascades regulate a variety of cellular activities, including cell growth, differentiation, survival, and death [30, 31]. Phosphorylation of p38 and JNK upon monocyte apoptosis was examined, and as shown in FIGS. 9b-c, p38 but not JNK, was phosphorylated following monocyte apoptosis. The phosphorylation was prolonged and not transient as seen following activation by LPS. IL-1-beta and IL-8 secretion was analyzed following apoptosis induction in the presence and absence of p38 and JNK inhibitors. As shown in FIGS. 9d and 9e, p38 inhibitor, but not JNK inhibitor, dramatically inhibited both IL-1-beta and IL-8 secretion.

In summary, pro-inflammatory IL-1-beta, IL-8, and MIP-1-alpha were all secreted at significant levels and in a transcriptional- and translational-dependent pattern in monocytes subjected to suspension-induced death. The cells showed a necrotic pattern with rapid lysis and their death was neither caspase- nor Fas-dependent.

Discussion: Apoptotic cells have been shown to signal neighboring cells in a variety of ways. Pro-phagocytic signals on apoptotic cells serve as markers for phagocytes to specifically recognize the apoptotic cells and subsequently ingest them. Such signals can appear on the membrane of apoptotic cells. Direct signals include alterations in cell surface phospholipid composition [32], changes in cell surface glycoproteins, or in surface charge [33]. Alternatively, certain serum proteins can opsonize an apoptotic cell surface, and signal to phagocytes to engulf the opsonized apoptotic cells [34, 35]. Similarly, viable cells express phagocytosis-inhibitory signals by restriction of phosphatidylserine to the inner leaflet of the plasma membrane or CD31 expression [36]. Apoptotic cells can also secrete molecules which are important for recruitment of phagocytic cells, phagocytosis, and immune responses in the immediate milieu Examples of mediators of immune suppression and phagocyte recruitment include TGF-beta [37] and phosphoisocholine [38]. Most of these mechanisms have suggested that there occurs efficient identification and clearance of apoptotic cells, in processes leading to non-inflammatory and non-autoimmune consequences [11, 12]. Yet the development of autoimmune diseases related to altered clearance of apoptotic cells, the phenomenon of cross-priming, and evidence that Fas signaling is associated with a pro-inflammatory response at least in some circumstances, suggest that a pro-inflammatory milieu is possible in the context of apoptosis. This raises the question of what would determine whether the consequence of monocyte death, either infected or not, may be anti-inflammatory or pro-inflammatory. The answer to that may be complicated, and dependent upon additional factors such as the presence of other cytokines/chemokines, heat-shock proteins, oxidation, necrosis rather than apoptosis, and triggering of pathogen associated molecular patterns (PAMPs). Monocytes were shown here to be capable of generating pro-inflammatory cytokines/chemokines when subjected to suspension-induced controlled necrosis. As such monocytes may have a unique and crucial role in host defense, in autoimmunity, and in the generation of inflammation. In monocytes, pro-inflammatory cytokines/chemokines may induce cross-priming, whereas anti-inflammatory cytokines may induce cross-tolerization.

Based on earlier studies, it was hypothesized that expression of Fas ligand (FasL) enables cells to counterattack the immune system, and that transplant rejection, for example, could be prevented by expressing Fas ligand on transplanted organs. More recent studies have indicated that the notion of Fas ligand as a mediator of immune privilege needed to be reconsidered, and in fact Fas ligation may be pro-inflammatory [28]. Indeed Fas was proposed to mediate pro-inflammatory cytokines such as IL-1-beta [39] and recently it has been suggested that, following anti-Fas (CH11)-induced apoptosis, human monocytes produced Fas-dependent IL-8 and TNF-alpha secretion, which was associated with NFkappaB activation, and was shown to occur in macrophages even in the absence of apoptosis [29].

The presently disclosed experimental results reveal for the first time a novel, non-Fas-dependent, non-caspase dependent pattern of pro-inflammatory cytokine/chemokine secretion that is associated with MAPK activation in monocytes subjected to suspension-induced controlled necrosis. In mammals MAPKs are divided into three major groups: ERKs, JNKs/stress-activated protein kinases, and p38, based on their degree of homology, biological activities, and phosphorylation motifs. JNK may contribute to death receptor transcription-dependent apoptotic signaling via c-Jun/AP-1, leading to transcriptional activation of FasL. Several studies suggested that the transcriptional activity of the c-Jun protein, which is increased by phosphorylation of c-Jun at $Ser^{63}$ and $Ser^{73}$ by JNK, is closely associated with apoptosis [40-42]. In this study only p38 was phosphorylated in association with apoptosis and showed sustained activation that differed from transient activation seen following exposure to LPS. This distinct pattern of non-Fas-dependent, serum-deprivation+suspension-induced monocyte apoptosis lead to pro-inflammatory secretion of cytokines and chemokines. Interestingly, although it is a distinct pattern, prolonged phosphorylation of JNK and p38 MAPK, accompanied by c-Jun/ATF-2 phosphorylation, preceded and triggered up-regulation of FasL, which in turn contributed to the apoptotic response [43]. In that regard, although no NFkappaB activation was documented and cytokine/chemokine secretion was not Fas-dependent, possible cross-talk in both pathways cannot be excluded.

It is not known in what physiological circumstances necrotic monocytes secrete pro-inflammatory cytokines either in Fas-dependent or p38-dependent patterns. Yet monocytes are unique among leukocytes in their p38-dependent cytokine/chemokine secretion, and as such sustained activation of p38 may determine immune response in homeostasis, infection, inflammation, and autoimmunity.

In summary, it is disclosed herein for the first time that human monocytes, but not neutrophils or resting B- or T-lymphocytes, undergo controlled necrosis and release high amounts of the pro-inflammatory cytokines IL-1-beta, IL-8, and MIP-1-alpha under non-substrate-adherent (suspension) conditions, and thereby create a pro-inflammatory milieu. Furthermore, it is shown that IL-1-beta secretion involves a signaling cascade that is completely distinct from the cascade seen upon monocyte activation or Fas signaling, is associated with p38 phosphorylation and is completely abrogated upon exposure of monocytes to p38 inhibitor. This distinct cascade may, on the one hand, help cross-priming upon infection, but on the other hand it may expose the body to persistent inflammatory and/or autoimmune response triggered by self-antigens that are derived from apoptotic monocytes in the context of pro-inflammatory cytokines and chemokines. Thus, it is disclosed herein for the first time that death of different freshly isolated leukocytes, such as neutrophils, monocytes, and lymphocytes, occurs via different modes and with different kinetics, under similar conditions, resulting in totally different immune responses.

Conclusion: The presently disclosed experimental results teach for the first time that ex-vivo suspension of monocytes, but not of other leukocytes, unexpectedly results in rapid necrosis and concomitant production of pro-inflammatory mediators, whereas subjecting monocytes to conditions facilitating their substrate-adherence results in their apoptosis with concomitant absence of secretion of pro-inflammatory mediators. These novel and unexpected discoveries can be exploited in various ways, particularly for improvement of suboptimal prior art apheresis procedures used in the treatment of inflammation-associated diseases, such as extracorporeal photopheresis for treatment of graft-versus-host disease, which involve ex-vivo suspension of monocytes, and their subsequent re-infusion. The presently disclosed results teach for the first time that such procedures are clearly suboptimal since they inherently involve the counter-productive introduction of pro-inflammatory mediators into patients being treated for inflammation-associated diseases, and that such prior art drawbacks can be avoided by subjecting the ex-vivo processed monocytes to substrate-adherent conditions instead of suspension.

Example 3

Therapeutic Usage of Apoptotic Lymphocytes

Apoptotic lymphocytes have an immunosuppressive, tolerizing, and anti-inflammatory effect provided they are isolated in the right way and therapeutically in the right conditions and if mixed with other cells, only in controlled way (which does not occur spontaneously in leukocytes from the blood). Described below are methods of suitably obtaining and administering apoptotic lymphocytes for treatment of various disease conditions.

Materials and Methods:
Generation of Apoptotic Lymphocytes:
1. Isolation of up to 1 billion PBMCs from up to 500 milliliters autologous blood, or up to 10 billion PBMCs by leukocyte apheresis.
2. Isolation of lymphocytes from PBMCs using magnetic beads conjugated to ligands of lymphocyte surface markers, or by subtraction of adherent lymphocytes.
4. Induction of lymphocyte apoptosis by one or more of the following methods:
  (i) serum withdrawal-induced apoptosis;
  (ii) irradiation-induced apoptosis using irradiation such as UV or gamma irradiation;
  (ii) chemically-induced apoptosis (using compounds such as staurosporine, cyclophosphamide, and hydrogen peroxide); and
  (iv) death receptor ligand-induced apoptosis.
5. Collection of up to 0.5 billion apoptotic lymphocytes using simple separation, and up to 5 billion apoptotic lymphocytes using leukocyte apheresis.
6. Therapeutic administration of apoptotic lymphocytes via one of the following routes: parenterally, intravenously, intramuscularly, subcutaneously, intra-dermally, and orally.
7. Repeat the procedure according to disease or indication.

Therapeutic Administration of Apoptotic Lymphocytes According to Disease/Indication:
The cell dosages described below are suitable for a 70 kg patient and may be adjusted according to body weight.
Anti-Inflammatory (and Anti-Thrombotic) Effect, Tolerance and Immunosuppression Induction:
1.1. Administer 10 million to 5 billion cells 24 hours prior to, and 24 hours following percutaneous transluminal coronary angioplasty (PTCA), such as with a stent or any other intravessel device or procedure to prevent restenosis. Administer 10 million to 5 billion cells 2 weeks later, as needed.

1.2. Administer 10 million to 5 billion cells during acute coronary event in order to reduce infarct size and reperfusion injury.

1.3. Administer 10 million to 5 billion cells during any vessel implantation of a stent in a similar protocol to 1.1.

1.4. Administer 10 million to 5 billion cells during acute thrombosis.

2.1. Prevention of solid organ rejection: Administer 10 million to 5 billion cells 2-24 hours prior to, and 24 hours following, solid organ transplantation. (2-24 hours before and 24 hours after). Administer 10 million to 5 billion cells every 2 weeks, as needed.

2.2. Prevention of heterologous bone marrow rejection: Administer 10 million to 5 billion cells 2-24 hours prior to, and 24 hours following, bone marrow transplantation. (2-24 hours before and 24 hours after). Administer 10 million to 5 billion cells every 2 weeks, as needed.

2.3. Prevention of GVHD.

2.3.1. Prophylactic treatment: Administer 10 million to 5 billion cells 2-24 hours prior to, and 24 hours following, transplantation. Administer 10 million to 5 billion cells every 2 weeks, as needed.

2.3.1. Treatment for overt GVHD: Administer 10 million to 5 billion cells every 2 weeks, as needed.

3.1. Treatment of Systemic Lupus Erythematosus (SLE):

3.1.1. Treatment of active disease: Administer 10 million to 5 billion cells every 2 weeks, as needed.

3.1.2. Prevention of flares: Administer 10 million to 5 billion cells every 2-4 weeks, as needed.

3.2. Treatment of autoimmune disease: Treatable autoimmune diseases include rheumatoid arthritis, idiopathic polyarthritis, multiple sclerosis, inflammatory bowel disease, scleroderma, Sjogren's syndrome, polymyositis or dermatomyositis, systemic or localized vasculitis, celiac disease, Guillain-Barre syndrome, myasthenia gravis, diabetes mellitus type I, antiphospholipid syndrome, thyroiditis. Grave's disease, and psoriasis. Can be used for treating active disease or preventing flares. Administer 10 million to 5 billion cells every 2-4 weeks, as needed.

4.1. Treatment of Chronic Inflammatory or Episodic Inflammation-Associated Illnesses Such as Familial Mediterranean Fever (FMF) and Other Periodic Fever Illnesses:

4.1.1. During attack, administer 10 million to 5 billion cells.

4.1.2. As prevention for attack, administer 10 million to 5 billion cells every 2 weeks, as needed.

4.1.3 Prevention of amyloidosis: Administer 10 million to 5 billion cells every 2-4 weeks, as needed.

Example 4

Therapeutic Usage of Apoptotic Monocytes

Apoptotic monocytes have an immunosuppressive, tolerizing, and anti-inflammatory effect provided they are isolated and therapeutically administered in the right way. Otherwise they may undergo pro-inflammatory necrosis. Described below are methods of suitably obtaining and administering apoptotic monocytes for treatment of various disease conditions.

Materials and Methods:

Generation of Apoptotic Monocytes:

1. Isolation of up to 1 billion PBMCs from up to 500 milliliters autologous blood, or up to 10 billion PBMCs by leukocyte apheresis.

2. Isolation of monocytes from PBMCs using either anti-CD14 antibody-conjugated magnetic beads, substrate-adherence or centrifugal elutriation.

3. Induction of adherence of monocytes (included in monocyte isolation performed via substrate adherence).

4. Induction of monocyte apoptosis by one or more of the following methods:
   (i) serum withdrawal-induced apoptosis;
   (ii) irradiation-induced apoptosis using irradiation such as UV or gamma irradiation;
   (ii) chemically-induced apoptosis (using compounds such as staurosporine, cyclophosphamide, and hydrogen peroxide); and
   (iv) death receptor ligand-induced apoptosis.

5. Collection of up to 120 million apoptotic monocytes using simple separation, and up to 1 billion apoptotic monocytes using leukocyte apheresis.

6. Washing and resuspension of the cells in physiological buffer.

7. Therapeutic administration of apoptotic lymphocytes via one of the following routes: parenterally, intravenously, intramuscularly, subcutaneously, intra-dermally, and orally.

8. Repeat the procedure according to disease or indication.

Therapeutic Administration of Apoptotic Monocytes According to Disease/Indication:

The cell dosages described below are suitable for a 70 kg patient and may be adjusted according to body weight.

Anti-Inflammatory (and Anti-Thrombotic) Effect, Tolerance and Immunosuppression Induction:

1.1. Administer 10 million to 1 billion cells 24 hours prior to, and 24 hours following percutaneous transluminal coronary angioplasty (PTCA), such as with a stent or any other intravessel device or procedure to prevent restenosis. Administer cells 2 weeks later, as needed.

1.2. Administer 10 million to 1 billion cells during acute coronary event in order to reduce infarct size and reperfusion injury.

1.3. Administer 10 million to 1 billion cells during any vessel implantation of a stent in a similar protocol to 1.1.

1.4. Administer 10 million to 1 billion cells during acute thrombosis.

2.1. Prevention of solid organ rejection: Administer 10 million to 1 billion cells 2-24 hours prior to, and 24 hours following, solid organ transplantation. (2-24 hours before and 24 hours after). Administer 10 million to 1 billion cells every 2 weeks, as needed.

2.2. Prevention of heterologous bone marrow rejection: Administer 10 million to 1 billion cells 2-24 hours prior to, and 24 hours following, bone marrow transplantation. (2-24 hours before and 24 hours after). Administer 10 million to 1 billion cells every 2 weeks, as needed.

2.3. Prevention of Graft-Versus-Host Disease (GVHD):

2.3.1. Prophylactic treatment: Administer 10 million to 1 billion cells 2-24 hours prior to, and 24 hours following, transplantation. Administer 10 million to 1 billion cells every 2 weeks, as needed.

2.3.1. Treatment for overt GVHD: Administer 10 million to 1 billion cells every 2 weeks, as needed.

3.1. Treatment of Systemic Lupus Erythematosus (SLE):

3.1.1. Treatment of active disease: Administer 10 million to 1 billion cells every 2 weeks, as needed.

3.1.2. Prevention of flares: Administer 10 million to 1 billion cells every 2-4 weeks, as needed.

3.2. Treatment of autoimmune disease: Treatable autoimmune diseases include rheumatoid arthritis, idiopathic polyarthritis, multiple sclerosis, inflammatory bowel disease, scleroderma, Sjogren's syndrome, polymyositis or dermatomyositis, systemic or localized vasculitis, celiac disease, Guillain-Barre syndrome, myasthenia gravis, diabetes mellitus type I, antiphospholipid syndrome, thyroiditis. Grave's disease, and psoriasis. Can be used for treating active disease or preventing flares. Administer 10 million to 1 billion cells every 2-4 weeks, as needed.

4.1. Treatment of Chronic Inflammatory or Episodic Inflammation-Associated Illnesses Such as Familial Mediterranean Fever (FMF) and Other Periodic Fever Illnesses:

4.1.1. During attack, administer 10 million to 1 billion cells.

4.1.2. As prevention for attack, administer 10 million to 1 billion cells every 2 weeks, as needed.

4.1.3 Prevention of amyloidosis: Administer 10 million to 1 billion cells every 2-4 weeks, as needed.

Example 5

Therapeutic Usage of Apoptotic Neutrophils

Apoptotic neutrophils have an immunosuppressive, tolerizing, and anti-inflammatory effect provided they are isolated in the right way and therapeutically administered in the right conditions and if mixed with other cells, only in controlled way (which does not occur spontaneously in leukocytes from the blood). Neutrophils contain proteases and other contents that may inhibit the anti-inflammatory, immunosuppressant effect if not administered correctly. Described below are methods of suitably obtaining and administering apoptotic neutrophils for treatment of various disease conditions.

Materials and Methods:

Generation of Apoptotic Neutrophils:

1. Isolation of up to 1 billion neutrophils from up to 500 milliliters autologous blood, or up to 10 billion neutrophils by neutrophil or leukocyte apheresis.

2. Induction of neutrophil apoptosis by one or more of the following methods (i) serum withdrawal-induced apoptosis;

(ii) irradiation-induced apoptosis using irradiation such as UV or gamma irradiation;

(ii) chemically-induced apoptosis (using compounds such as staurosporine, cyclophosphamide, and hydrogen peroxide); and (iv) death receptor ligand-induced apoptosis.

3. Collection of up to 0.5 billion apoptotic neutrophils using simple separation, and up to 5 billion apoptotic neutrophils using leukocyte apheresis.

4. Therapeutic administration of apoptotic neutrophils via one of the following routes: parenterally, intravenously, intramuscularly, subcutaneously, intra-dermally, and orally.

5. Repeat the procedure according to disease or indication.

Therapeutic Administration of Apoptotic Neutrophils According to Disease/Indication:

The cell dosages described below are suitable for a 70 kg patient and may be adjusted according to body weight.

Anti-Inflammatory (and Anti-Thrombotic) Effect, Tolerance and Immunosuppression Induction:

1.1. Administer 10 million to 5 billion cells 24 hours prior to, and 24 hours following percutaneous transluminal coronary angioplasty (PTCA), such as with a stent or any other intravessel device or procedure to prevent restenosis. Administer 10 million to 5 billion cells 2 weeks later, as needed.

1.2. Administer 10 million to 5 billion cells during acute coronary event in order to reduce infarct size and reperfusion injury.

1.3. Administer 10 million to 5 billion cells during any vessel implantation of a stent in a similar protocol to 1.1.

1.4. Administer 10 million to 5 billion cells during acute thrombosis.

2.1. Prevention of solid organ rejection: Administer 10 million to 5 billion cells 2-24 hours prior to, and 24 hours following, solid organ transplantation. (2-24 hours before and 24 hours after). Administer 10 million to 5 billion cells every 2 weeks, as needed.

2.2. Prevention of heterologous bone marrow rejection: Administer 10 million to 5 billion cells 2-24 hours prior to, and 24 hours following, bone marrow transplantation. (2-24 hours before and 24 hours after). Administer 10 million to 5 billion cells every 2 weeks, as needed.

2.3. Prevention of GVHD.

2.3.1. Prophylactic treatment: Administer 10 million to 5 billion cells 2-24 hours prior to, and 24 hours following, transplantation. Administer 10 million to 5 billion cells every 2 weeks, as needed.

2.3.1. Treatment for overt GVHD: Administer 10 million to 5 billion cells every 2 weeks, as needed.

3.1. Treatment of Systemic Lupus Erythematosus (SLE):

3.1.1. Treatment of active disease: Administer 10 million to 5 billion cells every 2 weeks, as needed.

3.1.2. Prevention of flares: Administer 10 million to 5 billion cells every 2-4 weeks, as needed.

3.2. Treatment of autoimmune disease: Treatable autoimmune diseases include rheumatoid arthritis, idiopathic polyarthritis, multiple sclerosis, inflammatory bowel disease, scleroderma, Sjogren's syndrome, polymyositis or dermatomyositis, systemic or localized vasculitis, celiac disease, Guillain-Barre syndrome, myasthenia gravis, diabetes mellitus type I, antiphospholipid syndrome, thyroiditis. Grave's disease, and psoriasis. Can be used for treating active disease or preventing flares. Administer 10 million to 5 billion cells every 2-4 weeks, as needed.

4.1. Treatment of Chronic Inflammatory or Episodic Inflammation-Associated Illnesses Such as Familial Mediterranean Fever (FMF) and Other Periodic Fever Illnesses:

4.1.1. During attack, administer 10 million to 5 billion cells.

4.1.2. As prevention for attack, administer 10 million to 5 billion cells every 2 weeks, as needed.

4.1.3 Prevention of amyloidosis: Administer 10 million to 5 billion cells every 2-4 weeks, as needed.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, and patents mentioned in this specification are herein incorporated in their entirety by reference into the specification, to the same extent as if each individual publication, or patent was specifically and individually indicated to be incorporated herein by reference. In addition, citation or identification of any reference in this application shall not be construed as an admission that such reference is available as prior art to the present invention.

What is claimed is:

1. A method of isolating and inducing apoptosis in a monocyte population, said method comprising isolating said monocytes by substrate adherence, and concurrently inducing apoptosis by subjecting said monocytes to in-vitro serum deprivation, wherein 70% of said resultant monocyte population is annexin positive and less than 5% is necrotic.

2. The method of claim 1, wherein said isolated, apoptotic monocytes are for use in treatment of inflammation-associated diseases.

* * * * *